「12」 United States Patent
Chen et al.

(10) Patent No.: US 10,392,643 B2
(45) Date of Patent: Aug. 27, 2019

(54) METHODS OF USING ACYL-COA SYNTHETASE FOR BIOSYNTHETIC PRODUCTION OF ACYL-COAS

(71) Applicant: Conagen Inc., Bedford, MA (US)

(72) Inventors: Hui Chen, Bedford, MA (US); Hongxue Wang, Jiangsu (CN); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 154 days.

(21) Appl. No.: 15/033,711

(22) PCT Filed: Nov. 3, 2014

(86) PCT No.: PCT/US2014/063695
§ 371 (c)(1),
(2) Date: May 2, 2016

(87) PCT Pub. No.: WO2015/066615
PCT Pub. Date: May 7, 2015

(65) Prior Publication Data
US 2016/0273014 A1 Sep. 22, 2016
US 2017/0247733 A2 Aug. 31, 2017

Related U.S. Application Data

(60) Provisional application No. 61/898,944, filed on Nov. 1, 2013.

(51) Int. Cl.
C12P 19/32 (2006.01)
C12P 7/64 (2006.01)

(52) U.S. Cl.
CPC ............. C12P 19/32 (2013.01); C12P 7/6436 (2013.01)

(58) Field of Classification Search
CPC combination set(s) only.
See application file for complete search history.

(56) References Cited

U.S. PATENT DOCUMENTS

| 7,759,548 | B2 | 7/2010 | Metz et al. |
| 2007/0220634 | A1 | 9/2007 | Metz |
| 2007/0244192 | A1 | 10/2007 | Metz |
| 2007/0245431 | A1 | 10/2007 | Metz et al. |
| 2007/0261138 | A1 | 11/2007 | Graham et al. |

FOREIGN PATENT DOCUMENTS

| CN | 103087998 A | 5/2013 |
| CN | 103725652 A | 4/2014 |
| JP | 2013-116104 A | 6/2013 |
| WO | WO 98/00557 A2 | 1/1998 |
| WO | WO 03/087321 A2 | 10/2003 |

OTHER PUBLICATIONS

ThaleMine AT4G23850—Gene LACS4. Retrieved from < https://apps.araport.org/thalemine/portal.do?externalids=AT4G23850 > on Apr. 1, 2018.*
Thiel et al., "Chili Pepper Fruits: Presumed Precursors of Fatty Acids Characteristic for Capsaicinoids", J. Agric. Food Chem. 2008, 56, 4219-4224.*
International Search Report and Written Opinion corresponding to International Patent Application No. PCT/US2014/63695, dated Apr. 22, 2015.
Aza-Gonzalez et al., Molecular biology of capsaicinoid biosynthesis in chili pepper (Capsicum spp.). Plant Cell Rep. May 2011, vol. 30, No. 5, p. 695-706.
Mazourek et al., A Dynamic Interface for Capsaicinoid Systems Biology, Plant Physiology, Aug. 2009, vol. 150, p. 1806, Table 1, p. 1816, para 3; Fig. 5.
Shockey et al., Arabidopsis Contains Nine Long-Chain Acyl-Coenzyme A Synthetase Genes That Participate in Fatty Acid and Glycerolipid Metabolism, Plant Physiology, Aug. 2002, vol. 129, pp. 1710. abstract p. 1713, para 1.
Geneseq database accession No. ADL 72268. Shockey et al. Oct. 23, 2003.
Geneseq database accession No. ADL 72357. Shockey et al. Oct. 23, 2003.
WPI database AN 2014-K94081. Apr. 16, 2014. CN 103 725 652 A.
Extended European Search Report EP Serial No. 14858891.6 dated Jun. 7, 2017.
Lee et al., Molecular cloning of a novel pathogen-inducible cDNA encoding a putative acyl-CoA synthetase from Capsicum annuum L. Plant Mol Biol. Aug. 2001;46(6):661-71.
Fujino et al., Molecular identification and characterization of two medium-chain acyl-CoA synthetases, MACS1 and the Sa gene product. J Biol Chem. Sep. 21, 2001;276(38):35961-6. Epub Jul. 24, 2001.

* cited by examiner

Primary Examiner — Suzanne M Noakes
(74) Attorney, Agent, or Firm — Wolf, Greenfield & Sacks, P.C.; Karen K. Chan

(57) ABSTRACT

A biosynthetic method of making carboxyl CoA from long-chain carboxylic acid including expressing an ACS in a cellular system, feeding a long-chain carboxylic acid to the cellular system, growing the cellular system in a medium, and producing carboxyl CoA.

5 Claims, 21 Drawing Sheets
Specification includes a Sequence Listing.

|  |  | 1 | 50 |
|---|---|---|---|
| CaSIG4 | (1) | GTGGGTATTGAATCTCTTATTCTTCGCCTATGGAGTGTTTGACGCTAACT | |
| Comp2147-1 | (1) | -------------------------------ATGGAGTGTTTGACGCTAACT | |
|  |  | 51 | 100 |
| CaSIG4 | (51) | GGATTCTTGAAACATGTGGCTGAAAAGTACCCTAGTCATCGTGCGATTTC | |
| Comp2147-1 | (22) | GGATTCTTGAAACATGTGGCTGAAAAGTACCCTAGTCATCGTGCGATTTC | |
|  |  | 101 | 150 |
| CaSIG4 | (101) | CGTTTCCGGCAGGCTCGATATCACTCATGCACGCCTTCAACAACTCGTTG | |
| Comp2147-1 | (72) | CGTTTCCGGCAGGCTCGATATCACTCATGCACGCCTTCAACAACTCGTTG | |
|  |  | 151 | 200 |
| CaSIG4 | (151) | AACGTGCCGCTTCTCAGATTGTAGCTGCCGGTGTAAAGCCTGGCGATGTC | |
| Comp2147-1 | (122) | AACGTGCCGCTTCTCAGATTGTAGCTGCCGGTGTAAAGCCTGGCGATGTC | |
|  |  | 201 | 250 |
| CaSIG4 | (201) | GTCGCTCTCACTTTCCCCAACACAATCGAGTTCGTGATCATGTTTTTAGC | |
| Comp2147-1 | (172) | GTCGCTCTCACTTTCCCCAACACAATCGAGTTCGTGATCATGTTTTTAGC | |
|  |  | 251 | 300 |
| CaSIG4 | (251) | TGTAATTCGAGCTCGAGCTACAGCAGCGCCACTGAATTCAGCGTACATGG | |
| Comp2147-1 | (222) | TGTAATTCGAGCTCGAGCTACAGCAGCGCCACTGAATTCAGCGTACATGG | |
|  |  | 301 | 350 |
| CaSIG4 | (301) | CAGAAGAATTCGAGTTTTATTTATCTGATTCAGAATCGAAACTCTTATTA | |
| Comp2147-1 | (272) | CAGAAGAATTCGAGTTTTATTTATCTGATTCAGAATCGAAACTCTTATTA | |
|  |  | 351 | 400 |
| CaSIG4 | (351) | ACTGCAAAAGAAGGAAACGAAGCAGCTCAAGCTGCTGCCTCCAAGCTAAA | |
| Comp2147-1 | (322) | ACTGCAAAAGAAGGAAACGAAGCAGCTCAAGCTGCTGCCTCCAAGCTAAA | |
|  |  | 401 | 450 |
| CaSIG4 | (401) | AATCCCTCGTATTAGTGTAACTCTCTCTCAACCCGACTCTGATGTCGCTT | |
| Comp2147-1 | (372) | AATCCCTCGTATTAGTGTAACTCTCTCTCAACCCGACTCTGATGTCGCTT | |
|  |  | 451 | 500 |
| CaSIG4 | (451) | TCTCCCCAGCTCCACCCGAATCGGACCTTGAATCGATGTCCAAAATCGTT | |
| Comp2147-1 | (422) | TCTCCCCTGCTCCACCCGAATCGGACCTTGAATCGATGTCCAAAATCGTT | |
|  |  | 501 | 550 |
| CaSIG4 | (501) | AACGAACCATCAGATGTTGGACTTTTCCTTCATACATCAGGCACCACTAG | |
| Comp2147-1 | (472) | AACGAACCATCAGATGTTGGACTTTTCCTTCATACATCAGGCACCACTAG | |
|  |  | 551 | 600 |
| CaSIG4 | (551) | CAGGCCAAAAGGTGTTCCTCTGGCTCAGCTGAATTTGTTGTCTTCAGTAA | |
| Comp2147-1 | (522) | CAGGCCAAAAGGTGTTCCTCTGTCTCAGCTGAATTTGTTGTCTTCAGTAA | |
|  |  | 601 | 650 |
| CaSIG4 | (601) | ACAATATCAAATCGGTGTACAAACTGAGTGACACGGATTCTACTGTGATT | |
| Comp2147-1 | (572) | GCAATATCAAATCGGTGTACAAACTGAGTGACACGGATTCTACTGTGATT | |
|  |  | 651 | 700 |
| CaSIG4 | (651) | GTGTTGCCGTTGTTTCACGTTCACGGGTTAATTGCGGGGTTACTGAGCTC | |
| Comp2147-1 | (622) | GTGTTGCCGTTGTTTCACGTTCACGGGTTAATTGCGGGGTTACTGAGCTC | |
|  |  | 701 | 750 |
| CaSIG4 | (701) | ACTTGGAGCCGGAGCAGCCGTGACACTTCCAGCTGCAGGGAGATTTTCAG | |
| Comp2147-1 | (672) | ACTTGGAGCCGGAGCAGCCGTGACACTTCCAGCTGCAGGGAGATTTTCAG | |
|  |  | 751 | 800 |
| CaSIG4 | (751) | CTTCGACTTTTTGGTCAGACATGAAAAAATACAACGCAACATGGTACACA | |
| Comp2147-1 | (722) | CTTCGACTTTTTGGTCAGACATGAAAAAATACAACGCAACATGGTACACA | |
|  |  | 801 | 850 |
| CaSIG4 | (801) | GCTGTGCCTACTATTCACCAAATTCTATTGGATCGTCACCTCAGCAAACC | |
| Comp2147-1 | (772) | GCTGTGCCTACAATTCACCAAATTCTATTGGATCGTCACCTCAGCAAACC | |
|  |  | 851 | 900 |
| CaSIG4 | (851) | CGAATCGGATTACCCAAAGCTTCGGTTCATTCGGAGCTGTAGTGCAGCAC | |
| Comp2147-1 | (822) | CGAATCGGATTACCCAAAGCTTCGGTTCATTCGGAGCTGTAGTGCAGCAC | |

FIG. 2A

```
                     901                                                 950
CaSIG4      (901)    TGGCTCCATCAGTGATGGCGCGGCTAGAAGAAGCATTCGCGGCTCCTGTT
Comp2147-1  (872)    TGGCTCCATCAGTGATGGCGCGGCTGGAAGAAGCATTCGGGGCTCCTGTT
                     951                                                1000
CaSIG4      (951)    TTGGAGGCGTATGCAATGACTGAGGCAACCCATTTGATGGCTTCGAACCC
Comp2147-1  (922)    TTGGAGGCGTATGCAATGACTGAGGCAACCCATTTGATGGCTTCGAACCC
                     1001                                               1050
CaSIG4      (1001)   CTTACCCGAGGATGGCCCACATATTCCCGGGTCAGTTGGGAAACCCGTGG
Comp2147-1  (972)    CTTACCCGAGGATGGCCCACATATTCCCGGGTCAGTTGGGAAACCCGTGG
                     1051                                               1100
CaSIG4      (1051)   GTCAAGAGATGGGCATTTTGAATGAGAATGGGGAGTTACAAGGGCCTAAT
Comp2147-1  (1022)   GTCAAGAGATGGGCATTTTGAATGAGAATGGGGAGTTACAAGGGCCTAAT
                     1101                                               1150
CaSIG4      (1101)   GCTAAAGGGGAAGTTTGTATAAGGGGTCCAAATGTGACAAAGGGATACAA
Comp2147-1  (1072)   GCTAAAGGGGAAGTTTGTATAAGGGGTCCAAATGTGACAAAGGGATACAA
                     1151                                               1200
CaSIG4      (1151)   GAACAATCCAGAGGCAAATAAATCAGCTTTCCAGTTTGGTTGGTTTCACA
Comp2147-1  (1122)   GAACAATCCAGAGGCAAATAAATCAGCTTTCCAGTTTGGTTGGTTTCACA
                     1201                                               1250
CaSIG4      (1201)   CTGGAGATGTGGGGTATTTGGACTCTGATGGATACTTGCATTTGGTTGGA
Comp2147-1  (1172)   CTGGAGATGTGGGGTATTTGGACTCTGATGGATACTTGCATTTGGTTGGA
                     1251                                               1300
CaSIG4      (1251)   AGAATCAAGGAGTTGATCAACCGCGGAGGGGAGAAAATATCACCTATTGA
Comp2147-1  (1222)   AGAATCAAGGAGTTGATCAACCGCGGAGGGGAGAAAATATCACCTATTGA
                     1301                                               1350
CaSIG4      (1301)   ATTGGATGCAGTCCTAGTTTCTCATCCAGAAATTGCTCAGGCTGTTGCTT
Comp2147-1  (1272)   ATTGGATGCAGTCCTAGTTTCTCATCCAGAAATTGCTCAGGCTGTTGCTT
                     1351                                               1400
CaSIG4      (1351)   TTGGAGTCCCTGACGACAAGTATGGTGAAGAGATAAACTGTGCAGTTATT
Comp2147-1  (1322)   TTGGAGTCCCTGACGACAAGTATGGTGAAGAGATAAACTGTGCAGTTATT
                     1401                                               1450
CaSIG4      (1401)   CCAAGAGAAGGGTCAAACATCGATGAAGCAGAGGTGCTGAGATTTTGCAA
Comp2147-1  (1372)   CCAAGAGAAGGGTCAAACATCGATGAAGCAGAGGTGCTGAGATTTTGCAA
                     1451                                               1500
CaSIG4      (1451)   GAAGAATTTGGCAGCCTTTAAGGTCCCAAAGAAGGTCTTCATGACTGATT
Comp2147-1  (1422)   GAAGAATTTGGCAGCCTTTAAGGTCCCAAAGAAGGTCTTCATGACTGATT
                     1501                                               1550
CaSIG4      (1501)   CTCTTCCAAAAACTGCATCAGGAAAAATTCAACGCCGACTCGTTGCAGAG
Comp2147-1  (1472)   CTCTTCCAAAAACTGCATCAGGAAAAATTCAACGCCGACTCGTTGCAGAG
                     1551                                               1600
CaSIG4      (1551)   CACTTCCTTGCACAGATTTCAACTGCTAAAGTCCCCAAGTTTGGAGCATA
Comp2147-1  (1522)   CACTTCCTTGCACAGATTTCAACTGCTAAAGTCCCCAAGTTTGGAGCATA
                     1601                                               1650
CaSIG4      (1601)   GAAAAATTGTTGGCTATCTACGATTCCTTCTCCTATTAACAATAATAAAA
Comp2147-1  (1572)   G-------------------------------------------------
                     1651                                               1700
CaSIG4      (1651)   ATGTGCTTTTCGATATTACTTACGTACCATACTACTTGGTCAAGAAATCG
Comp2147-1  (1573)   --------------------------------------------------
                     1701                                               1750
CaSIG4      (1701)   GGACACGAGAATATATCAGTGCCTCTAGATTTTCAGTAATGGCGCAAGTA
Comp2147-1  (1573)   --------------------------------------------------
                     1751                                               1800
CaSIG4      (1751)   TATTCTCTTATAGTCTTTTCAGGGTAGATATTTTGTATTTCTCTACTTAG
Comp2147-1  (1573)   --------------------------------------------------
                     1801                                               1850
CaSIG4      (1801)   TATTGCAAAGGTTCTTTTATTTGTAAGTTGTGACAATGCCTTGGACAAAT
Comp2147-1  (1573)   --------------------------------------------------
```

FIG. 2B

```
                    1851                                              1900
     CaSIG4   (1851) GAATGAAAGTGCAGTTTGTAAGGCCCTTATTTAAAAAAAAAAAAAAAAAA
Comp2147-1   (1573) --------------------------------------------------
```

FIG. 2C

|  |  | 1 | 50 |
|---|---|---|---|
| ACS1 | (1) | ATGGCAACAGATAAATTTATTATTGAAGTTGAATCAGCAAAACCTGCTAA | |
| comp66462_c0_seq1 | (1) | ATGGCAACAGATAAATTTATTATTGAAGTTGAATCAGCAAAACCTGCTAA | |
| comp79520_c0_seq1 | (1) | -------------------------------------------------- | |
|  |  | 51 | 100 |
| ACS1 | (51) | AGATGGAAGACCATCAATGGGTCCTGTTTATAGAAGTATTTTTGCTAAAC | |
| comp66462_c0_seq1 | (51) | AGATGGAAGACCATCAATGGGTCCTGTTTATAGAAGTATTTTTGCTAAAC | |
| comp79520_c0_seq1 | (1) | -------------------------------------------------- | |
|  |  | 101 | 150 |
| ACS1 | (101) | ATGGATTTCCTCCACCTATTCCTGGGCTTGATAGTTGCTGGGATATTTTT | |
| comp66462_c0_seq1 | (101) | ATGGATTTCCTCCACCTATTCCTGGGCTTGATAGTTGCTGGGATATTTTT | |
| comp79520_c0_seq1 | (1) | -------------------------------------------------- | |
|  |  | 151 | 200 |
| ACS1 | (151) | CGTATGTCAGTGGAGAAATATCCTAACAATCGGATGCTTGGACGCCGTGA | |
| comp66462_c0_seq1 | (151) | CGTATGTCAGTGGAGAAATATCCTAACAATCGGATGCTTGGACGCCGTGA | |
| comp79520_c0_seq1 | (1) | -------------------------------------------------- | |
|  |  | 201 | 250 |
| ACS1 | (201) | GATTGTAGATGGAAAACCTGGCAAGTATGTGTGGATGTCTTACAAAGAAG | |
| comp66462_c0_seq1 | (201) | GATTGTAGATGGAAAACCTGGCAAGTATGTGTGGATGTCTTACAAAGAAG | |
| comp79520_c0_seq1 | (1) | -------------------------------------------------- | |
|  |  | 251 | 300 |
| ACS1 | (251) | TTTATGACATTGTGATTAAAGTAGGAAATTCCATCCGGAGCATTGGTGTG | |
| comp66462_c0_seq1 | (251) | TTTATGACATTGTGATTAAAGTAGGAAATTCCATCCGGAGCATTGGTGTG | |
| comp79520_c0_seq1 | (1) | -------------------------------------------------- | |
|  |  | 301 | 350 |
| ACS1 | (301) | GATGTGGGAGACAAATGTGGTATCTATGGTGCCAATTGCCCTGAGTGGAT | |
| comp66462_c0_seq1 | (301) | GATGTGGGAGACAAATGTGGTATCTATGGTGCCAATTGCCCTGAGTGGAT | |
| comp79520_c0_seq1 | (1) | -------------------------------------------------- | |
|  |  | 351 | 400 |
| ACS1 | (351) | AATAAGCATGGAGGCATGCAATGCTCATGGACTTTACTGTGTTCCTCTGT | |
| comp66462_c0_seq1 | (351) | AATAAGCATGGAGGCATGCAATGCTCATGGACTTTACTGTGTTCCTCTGT | |
| comp79520_c0_seq1 | (1) | -------------------------------------------------- | |
|  |  | 401 | 450 |
| ACS1 | (401) | ATGACACCTTAGGTGCTGGTGCTGTGGAATTTATCATTTCCCATGCTGAG | |
| comp66462_c0_seq1 | (401) | ATGACACCTTAGGTGCTGGTGCTGTGGAATTTATCATTTCCCATGCTGAG | |
| comp79520_c0_seq1 | (1) | -------------------------------------------------- | |
|  |  | 451 | 500 |
| ACS1 | (451) | GTTACAATTGCTTTTGTTGAAGAGAAAAAACTTCCTGAGCTTCTGAAAAC | |
| comp66462_c0_seq1 | (451) | GTTACAATTGCTTTTGTTGAAGAGAAAAAACTTCCTGAGCTTCTGAAAAC | |
| comp79520_c0_seq1 | (1) | -------------------------------------------------- | |
|  |  | 501 | 550 |
| ACS1 | (501) | TTTTCCAAATGCGTCAAAGTACTTGAAAACTATTGTGAGTTTCGGAAAGG | |
| comp66462_c0_seq1 | (501) | TTTTCCAAATGCGTCAAAGTACTTGAAAACTATTGTGAGTTTCGGAAAGG | |
| comp79520_c0_seq1 | (1) | -------------------------------------------------- | |
|  |  | 551 | 600 |
| ACS1 | (551) | TCACTCCTGAACAGAAAAAAGAGCTTGAAGAGTTTGGGGTGGTTCTTTAC | |
| comp66462_c0_seq1 | (551) | TCACTCCTGAACAGAAAAAAGAGCTTGAAGAGTTTGGGGTGGTTCTTTAC | |
| comp79520_c0_seq1 | (1) | -------------------------------------------------- | |
|  |  | 601 | 650 |
| ACS1 | (601) | TCGTGGGATGAGTTTCTTCAATTGGGAAGCGGAAAACAATTTGATCTTCC | |
| comp66462_c0_seq1 | (601) | TCGTGGGATGAGTTTCTTCAATTGGGAAGCGGAAAACAATTTGATCTTCC | |
| comp79520_c0_seq1 | (1) | -------------------------------------------------- | |
|  |  | 651 | 700 |
| ACS1 | (651) | AGTGAAAAAGAAGGAAGACATCTGTACAATAATGTATACTAGTGGAACGA | |
| comp66462_c0_seq1 | (651) | AGTGAAAAAGAAGGAAGACATCTGTACAATAATGTATACTAGTGGAACGA | |
| comp79520_c0_seq1 | (1) | -------------------------------------------------- | |
|  |  | 701 | 750 |

FIG. 3A

```
             ACS1    (701) CCGGAGACCCCAAAGGTGTCCTGATTTCAAATACTAGCATTGTTACTCTT
    comp66462_c0_seq1 (701) CCGGAGACCCCAAAGGTGTCCTGATTTCAAATACTAGCATTGTTACTCTT
    comp79520_c0_seq1   (1) --------------------------------------------------
                            751                                             800
             ACS1    (751) ATAGCTGGAGTAAGGCGTTTCCTTGGGAGCGTGGATGAGTCGTTGAATGT
    comp66462_c0_seq1 (751) ATAGCTGGAGTAAGGCGTTTCCTTGGGAGCGTGGATGAGTCGTTGAATGT
    comp79520_c0_seq1   (1) --------------------------------------------------
                            801                                             850
             ACS1    (801) GGACGATGTGTATCTTTCGTATCTTCCCCTGGCACATATCTTTGATCGAG
    comp66462_c0_seq1 (801) GGACGATGTGTATCTTTCGTATCTTCCCCTGGCACATATCTTTGATCGAG
    comp79520_c0_seq1   (1) --------------------------------------------------
                            851                                             900
             ACS1    (851) TGATTGAAGAGTGTTTCATTCATCATGGTGCCTCGATAGGATTTTGGCGA
    comp66462_c0_seq1 (851) TGATTGAAGAGTGTTTCATTCATCATGGTGCCTCGATAGGATTCTGGCGA
    comp79520_c0_seq1   (1) --------------------------------------------------
                            901                                             950
             ACS1    (901) GGGGATGTCAAGTTACTAACCGAAGATATTGGAGAACTGAAACCAACTGT
    comp66462_c0_seq1 (901) GGGGATGTCAAGTTACTAACCGAAGATATTGGAGAACTGAAACCAACCGT
    comp79520_c0_seq1   (1) --------------------------------------------------
                            951                                            1000
             ACS1    (951) CTTCTGTGCTGTACCTCGGGTACTAGACAGAATATATTCAGGTTTGCAAC
    comp66462_c0_seq1 (951) CTTCTGTGCTGTACCTCGGGTACTAGACAGAATATATTCAGGTTTGCAAC
    comp79520_c0_seq1   (1) --------------------------------------------------
                            1001                                           1050
             ACS1   (1001) AGAAAATTGCTGCTGGTGGTTTTCTCAAAAGCACGTTGTTCAATCTTGCC
    comp66462_c0_seq1(1001) AGAAAATTGCTGCTGGTGGTTTTCTCAAAAGCACGTTGTTCAATCTTGCC
    comp79520_c0_seq1   (1) --------------------------------------------------
                            1051                                           1100
             ACS1   (1051) TATGCTTACAAACACCACAATTTGAAGAAGGGGCGTAAACACTTTGAAGC
    comp66462_c0_seq1(1051) TATGCTTACAAACACCACAATTTGAAGAAGGGGCGTAAACACTTTGAAGC
    comp79520_c0_seq1   (1) --------------------------------------------------
                            1101                                           1150
             ACS1   (1101) TTCTCCGCTTTCTGACAAAGTTGTCTTCAGTAAGGTAAAAGAAGGGTTAG
    comp66462_c0_seq1(1101) TTCTCCGCTTTCTGACAAAGTTGTCTTCAGTAAGGTAAAAGAAGGGTTAG
    comp79520_c0_seq1   (1) --------------------------------------------------
                            1151                                           1200
             ACS1   (1151) GAGGCAGAGTACGACTTATATTGTCTGGAGCAGCGCCCCTTGCAGCTCAT
    comp66462_c0_seq1(1151) GAGGCAGAGTACGACTTATATTGTCTGGAGCAGCGCCCCTTGCAGCTCAT
    comp79520_c0_seq1   (1) --------------------------------------------------
                            1201                                           1250
             ACS1   (1201) GTGGAAGCTTTTTGCGAGTTGTGGCATGCTGTCACGTTCTTCAAGGATA
    comp66462_c0_seq1(1201) GTGGAAGCTTTTTGCGAGTTGTGGCATGCTGTCACGTTCTTCAAGGATA
    comp79520_c0_seq1   (1) --------------------------------------------------
                            1251                                           1300
             ACS1   (1251) TGGTTTGACTGAAACGTGTGCTGGTACATTTGTGTCGCTACCCAACCGGT
    comp66462_c0_seq1(1251) TGGTTTGACTGAAACGTGTGCTGGTACATTTGTGTCGCTACCCAACCGGT
    comp79520_c0_seq1   (1) --------------------------------------------------
                            1301                                           1350
             ACS1   (1301) ATGATATGCTTGGTACGGTTGGTCCTCCCGTGCCCAACGTGGATGTGTGC
    comp66462_c0_seq1(1301) ATGATATGCTTGGTACGGTTGGTCCTCCCGTGCCCAACGTGGATGTGTGC
    comp79520_c0_seq1   (1) --------------------------------------------------
                            1351                                           1400
             ACS1   (1351) TTGGAGTCCGTTCCTGAAATGTCATATGATGCTTTGTCAAGCACGCCACG
    comp66462_c0_seq1(1351) TTGGAGTCCGTTCCTGAAATGTCATATGATGCTTTGTCAAGCACGCCACG
    comp79520_c0_seq1   (1) --------------------------------------------------
                            1401                                           1450
             ACS1   (1401) TGGAGAAGTGTGTGTGAGGGGGGACATTCTATTTTCAGGCTATTACAAGC
```

FIG. 3B

```
comp66462_c0_seq1  (1401) TGGAGAAGTGTGTGTGAGGGGGGACGTTCTATTTTCAGGCTATTACAAGC
comp79520_c0_seq1     (1) --------------------------------------------------
                          1451                                          1500
             ACS1  (1451) GTGAGGACCTAACGAAAGAAGTCATGATTGATGGGTGGTTTCACACAGGT
comp66462_c0_seq1  (1451) GTGAGGACCTAACAAAAGAAGTCATGATTGATGGGTGGTTTCACACAGGT
comp79520_c0_seq1     (1) -------------------------------------------CACAGGT
                          1501                                          1550
             ACS1  (1501) GATGTTGGCGAGTGGCAACCTAACGGTAGCTTGAAAATAATTGACCGCAA
comp66462_c0_seq1  (1501) GATGTTGGCGAGTGG-----------------------------------
comp79520_c0_seq1     (8) GATGTTGGCGAGTGGCAACCTAACGGTAGCTTGAAAATAATTGACCGCAA
                          1551                                          1600
             ACS1  (1551) GAAGAACATTTTCAAGCTCTCACAAGGTGAATATGTGGCTGTCGAAAATC
comp66462_c0_seq1  (1516) --------------------------------------------------
comp79520_c0_seq1    (58) GAAGAACATTTTCAAGCTCTCACAAGGTGAATATGTTGCTGTCGAAAATC
                          1601                                          1650
             ACS1  (1601) TGGAGAATATCTATGGCAATAATCCTATTATTGACTCGATATGGATATAC
comp66462_c0_seq1  (1516) --------------------------------------------------
comp79520_c0_seq1   (108) TGGAGAATATCTATGGCAATAATCCTATTATTGACTCGATATGGATATAC
                          1651                                          1700
             ACS1  (1651) GGGAACAGTTTCGAGTCCTTCCTTGTTGCTGTTATTAACCCAAACCAACG
comp66462_c0_seq1  (1516) --------------------------------------------------
comp79520_c0_seq1   (158) GGGAACAGTTTCGAGTCCTTCCTTGTTGCTGTTATTAACCCAAACCAACG
                          1701                                          1750
             ACS1  (1701) AGCAGTTGAACAATGGGCCGAAGTTAATGGCTTGTCTGGGGATTTTGCTT
comp66462_c0_seq1  (1516) --------------------------------------------------
comp79520_c0_seq1   (208) AGCAGTTGAACAATGGGCCGAAGTTAATGGCTTGTCTGGGGGTTTTGCTT
                          1751                                          1800
             ACS1  (1751) CCTTGTGTGAAAAGCCGGAAGTGAAAGAGTACATACTTCGAGAGCTAACA
comp66462_c0_seq1  (1516) --------------------------------------------------
comp79520_c0_seq1   (258) CCTTGTGTGAAAAGCCGGAAGTGAAAGAGTACATACTTCGAGAGCTAACA
                          1801                                          1850
             ACS1  (1801) AAAACCGGAAAAGAAAAGAAGTTGAAGGGCTTTGAGTTCCTAAAAGCGGT
comp66462_c0_seq1  (1516) --------------------------------------------------
comp79520_c0_seq1   (308) AAAACCGGAAAAGAAAAGAAGTTGAAGGGCTTTGAGTTCCTAAAAGCGGT
                          1851                                          1900
             ACS1  (1851) ACACCTTGATCCTGTGCCATTCGACATGGAACGAGACCTTCTAACTCCGA
comp66462_c0_seq1  (1516) --------------------------------------------------
comp79520_c0_seq1   (358) ACACCTTGATCCTGTGCCATTCGACATGGAACGAGACCTTCTAACTCCGA
                          1901                                          1950
             ACS1  (1901) CATTCAAGAAGAAAGACCCCAATTGCTCAAATACTACAAGGATGTGATT
comp66462_c0_seq1  (1516) --------------------------------------------------
comp79520_c0_seq1   (408) CATTCAAGAAGAAAGACCCCAATTGCTCAAATACTAC-------------
                          1951           1977
             ACS1  (1951) GACAGCATGTACAAGGGTACCAAGTGA
comp66462_c0_seq1  (1516) ---------------------------
comp79520_c0_seq1   (446) ---------------------------
```

FIG. 3C

|                    |       | 1                                                    50 |
|---|---|---|
| ACS2               | (1)   | ATGGAAGATTCTGAGGGAAGTAATCCATATACGAGTTCAGTGGAGAGACT |
| comp167_c0_seq1    | (1)   | -------------------------------------------------- |
| comp46218_c0_seq1  | (1)   | -------------------AATCCATATACGAGTACAGTGGAGAGACT |
|                    |       | 51                                                  100 |
| ACS2               | (51)  | GACCAGCTATGATTATATCTCCAAAAATTATGGGTCATCTGGGGTTACTG |
| comp167_c0_seq1    | (1)   | -------------------------------------------------- |
| comp46218_c0_seq1  | (30)  | GACCAGCTATGATTATATCTCCAAAAATTATGGGTCATCTGGGGTTACTG |
|                    |       | 101                                                 150 |
| ACS2               | (101) | GTGCAGTTTTTATTGCCATTATTATGCCAATAATCCTCTCCATGTTACTT |
| comp167_c0_seq1    | (1)   | -------------------------------------------------- |
| comp46218_c0_seq1  | (80)  | GTGCAGTTTTTATTGCCATTATTATGCCAATAATCCTCTCCATGTTACTT |
|                    |       | 151                                                 200 |
| ACS2               | (151) | ATGGGGAAGAAGAAGGCAAAACAGAGAGGTGTTCCGGTTCAAGTTGGTGG |
| comp167_c0_seq1    | (1)   | -------------------------------------------------- |
| comp46218_c0_seq1  | (130) | ATGGGGAAGAAGAAGGCAAAACAGAGAGGTGTTCCGGTTCAAGTTGGTGG |
|                    |       | 201                                                 250 |
| ACS2               | (201) | TGAGGCAGGTCTTGCAATGCGCAATGTTAAATCAGCAAGATTAGTTGAAG |
| comp167_c0_seq1    | (1)   | -------------------------------------------------- |
| comp46218_c0_seq1  | (180) | TGAGGCAGGTCTTGCAATGCGCAATGTTAAATCAGCAAGATTAGTTGAAG |
|                    |       | 251                                                 300 |
| ACS2               | (251) | TTCCTTGGGAAGGGGCTACAACTGTACCAGCTCTATTTGAGCAGTCTTGC |
| comp167_c0_seq1    | (1)   | -------------------------------------------------- |
| comp46218_c0_seq1  | (230) | TTCCTTGGGAAGGGGCTACAACTGTACCAGCTCTATTTGAGCAGTCTTGC |
|                    |       | 301                                                 350 |
| ACS2               | (301) | AAAAAACATTCTTCTGATCGCTGTCTTGGAACTAGAAAACTAGTTAGCAG |
| comp167_c0_seq1    | (1)   | -------------------------------------------------- |
| comp46218_c0_seq1  | (280) | AAAAAACATTCTTCTGATCGCTGTCTTGGAACTAGAAAACTAGTTAGCAG |
|                    |       | 351                                                 400 |
| ACS2               | (351) | GGACTTTGTTACTGCAAGTGATGGAAGGAAGTTTGAGAAACTTCACTTGG |
| comp167_c0_seq1    | (1)   | -------------------------------------------------- |
| comp46218_c0_seq1  | (330) | GGACTTTGTTACTGCAAGTGATGGAAGGAAGTTTGAGAAACTTCACTTGG |
|                    |       | 401                                                 450 |
| ACS2               | (401) | GGGAGTATCAGTGGGAATCTTATGGACAAGTATTTGATCGCACTTGCAAC |
| comp167_c0_seq1    | (1)   | -------------------------------------------------- |
| comp46218_c0_seq1  | (380) | GGGAGTATCAGTGGGAATCTTATGGACAAGTATTTGATCGCACTTGCAAC |
|                    |       | 451                                                 500 |
| ACS2               | (451) | TTTGCCTCTGGTCTTATTAAATTTGGTCATGATGTGGACACTCACGCTGC |
| comp167_c0_seq1    | (1)   | -------------------------------------------------- |
| comp46218_c0_seq1  | (430) | TTTGCCTCTGGTCTTATTAAATTTGGTCATGATGTGGACACTCACGCTGC |
|                    |       | 501                                                 550 |
| ACS2               | (501) | TATCTGTGCAGAAACTCGTCCAGAGTGGATCATTGCCTTTCAGGGATGCT |
| comp167_c0_seq1    | (1)   | -------------------------------------------------- |
| comp46218_c0_seq1  | (480) | TATCTTTGCAGAAACTCGTCCAGAGTGGATCATTGCCTTTCAGGGATGCT |
|                    |       | 551                                                 600 |
| ACS2               | (551) | TCCGGCAGAATATTACTGTTGTTACCATTTATGCTTCCTTGGGTGATGAT |
| comp167_c0_seq1    | (1)   | -------------------------------------------------- |
| comp46218_c0_seq1  | (530) | TCCGGCAGAATGTTACTGTTGTTACCATTTATGCTTCCTTGGGTGATGAT |
|                    |       | 601                                                 650 |
| ACS2               | (601) | GCACTCATTCATTCACTCAATGAGACCCAAGTATCTACATTGATATGTGA |
| comp167_c0_seq1    | (1)   | -------------------------------------------------- |
| comp46218_c0_seq1  | (580) | GCACTCATTCATTCACTCAATGAGACCCAAGTATCTACATTGATATGTGA |
|                    |       | 651                                                 700 |
| ACS2               | (651) | TGCCAAGCAACTGAAAAAGTGGCTTCTGTTAGTTCGAGCCTGAAAACCA |
| comp167_c0_seq1    | (1)   | -------------------------------------------------- |
| comp46218_c0_seq1  | (630) | TGCCAAGCAACTGAAAAAGTGGCTTCTGTTAGTTCGAGCCTGAAAACCA |
|                    |       | 701                                                 750 |

FIG. 4A

```
          ACS2    (701)  TCAAGAATGTCATCTATTTTGAGGATGACGAGACGGCAATAGATTCCACA
    comp167_c0_seq1    (1)  --------------------------------------------------
comp46218_c0_seq1  (680)  TCAAGAATGTCATCTATTTTGAGGATGACGAGACGGCAATAGATTCCACA
                           751                                            800
          ACS2    (751)  AATATTGACAGCTGGAGGATGTCGTCTTTCTCAGCAGTTGAAAAGCTGGG
    comp167_c0_seq1    (1)  ------------------------------------------AGCTGGG
comp46218_c0_seq1  (730)  AATATTGACAGCTGGAGGATGTCGTCTTTCTCAGCAGTTGAAAAGCTGGG
                           801                                            850
          ACS2    (801)  TAAAAATAGTCCTATTCAGCCAAGACTGCCTATCAAAGAAGATATTGCTG
    comp167_c0_seq1    (8)  TAAAAATAGTCCTATTCGGCCAAGACTGCCTATCAAAGAAGATATTGCTG
comp46218_c0_seq1  (780)  TAAAAATAGTCCTATTCAGCCAAGACTGC---------------------
                           851                                            900
          ACS2    (851)  TGATCATGTATACAAGTGGCAGTACAGGCTTGCCTAAGGGTGTTATGATA
    comp167_c0_seq1   (58)  TGATCATGTATACAAGTGGCAGTACAGGCTTGCCTAAGGGTGTTATGATA
comp46218_c0_seq1  (809)  --------------------------------------------------
                           901                                            950
          ACS2    (901)  ACTCATGGAAACATTGTAGCCACTTCAGCTGCTGTTATGACTGTGATTCC
    comp167_c0_seq1  (108)  ACTCATGGAAACATTGTAGCCACTTCAGCTGCTGTTATGACTGTGATTCC
comp46218_c0_seq1  (809)  --------------------------------------------------
                           951                                           1000
          ACS2    (951)  GAACCTTGGAAGCAGTGATGTGTATTTGGCTTACCTTCCTTTAGCTCACG
    comp167_c0_seq1  (158)  AAACCTTGGAAGCAGTGATGTGTATTTGGCTTACCTTCCTTTAGCTCACG
comp46218_c0_seq1  (809)  --------------------------------------------------
                          1001                                           1050
          ACS2   (1001)  TTTTTGAGCTAGCTGCCGAGACCGTAATGTTGACTGCAGGTGCTTGTATT
    comp167_c0_seq1  (208)  TTTTTGAGCTAGCTGCCGAGACCGTAATGTTGACTGCAGGTGCTTGTATT
comp46218_c0_seq1  (809)  --------------------------------------------------
                          1051                                           1100
          ACS2   (1051)  GGTTATGGCTCAGCTCTCACATTGACGGACACTTCTAACAAAGTCATGAA
    comp167_c0_seq1  (258)  GGTTATGGCTCAGCTCTCACATTGACGGACACTTCTAACAAAGTCATGAA
comp46218_c0_seq1  (809)  --------------------------------------------------
                          1101                                           1150
          ACS2   (1101)  GGGGACCAAGGGAGATGCTACAGTTTTAAAACCTACTTTAATGGCAGCAG
    comp167_c0_seq1  (308)  GGGGACCAAGGGAGATGCTACAGTTTTAAAACCTACTTTAATGGCAGCAG
comp46218_c0_seq1  (809)  --------------------------------------------------
                          1151                                           1200
          ACS2   (1151)  TTCCAGCCATTCTGGATCGTGTTCGGGATGGTGTTATGAAGAAGGTTGAG
    comp167_c0_seq1  (358)  TTCCAGCCATTCTGGATCGTGTTCGGGATGGTGTTATGAAGAAGGTTGAG
comp46218_c0_seq1  (809)  --------------------------------------------------
                          1201                                           1250
          ACS2   (1201)  GAGAAGGCAGGTTCTGCCAAGAAACTTTTCCACATTGGCTTTAACCGTCG
    comp167_c0_seq1  (408)  GAGAAGGCAGGTTCTGCCAAGAAACTTTTCCACATTGGCTTTAACCGTCG
comp46218_c0_seq1  (809)  --------------------------------------------------
                          1251                                           1300
          ACS2   (1251)  ATTGGCTGCTATGGAAGGTAGCTGGTTTGGAGCTTGGGGTCTAGAGAAAC
    comp167_c0_seq1  (458)  ATTGGCTGCTATGGAAGGTAGCTGGTTTGGAGCTTGGGGTCTAGAGAAAC
comp46218_c0_seq1  (809)  --------------------------------------------------
                          1301                                           1350
          ACS2   (1301)  AATTGTGGGATATCATTATATTTAAAAAGGTGAGGGCTGTGCTTGGCGGA
    comp167_c0_seq1  (508)  AATTGTGGGATATCATTATATTTAAAAAGGTGAGGGCTGTGCTTGGCGGA
comp46218_c0_seq1  (809)  --------------------------------------------------
                          1351                                           1400
          ACS2   (1351)  GATATCCGTTTCATGCTTTGCGGTGGTGCTCCTCTATCAGGAGATACTCA
    comp167_c0_seq1  (558)  GATATCCGTTTCATGCTTTGCGGTGGTGCTCCTCTATCAGGAGATACTCA
comp46218_c0_seq1  (809)  --------------------------------------------------
                          1401                                           1450
          ACS2   (1401)  AAGATTTATCAACATTTGTATGGGAGCTCCTATTGGTCAAGGGTATGGCT
```

FIG. 4A (continued)

```
comp167_c0_seq1   (608)  AAGATTTATCAACATTTGTATGGGAGCTCCTATTGGTCAAGGGTATGGCT
comp46218_c0_seq1 (809)  --------------------------------------------------
                          1451                                          1500
             ACS2 (1451) TGACAGAAACATTTGCTGGAGCTACTTTCTCTGAGTGGGATGATCCTTCT
comp167_c0_seq1   (658)  TGACAGAAACATTTGCTGGAGCTACTTTCTCTGAGTGGGATGATCCTTCT
comp46218_c0_seq1 (809)  --------------------------------------------------
                          1501                                          1550
             ACS2 (1501) GTTGGGCGTGTTGGTCCACCTCTTCCTTGTTCCTACATAAAGCTTGTTAC
comp167_c0_seq1   (708)  GTTGGGCGTGTTGGTCCACCTCTTCCTT----------------------
comp46218_c0_seq1 (809)  --------------------------------------------------
                          1551                                          1600
             ACS2 (1551) TTGGGAAGAAGGAGGTTACAGAATAGTTGATAAGCCTATGCCTCGGGGGG
comp167_c0_seq1   (736)  --------------------------------------------------
comp46218_c0_seq1 (809)  --------------------------------------------------
                          1601                                          1650
             ACS2 (1601) AAGTAGTTGTTGGTGGATGCAGCATCACTGCTGGTTACTTCAACAATGAG
comp167_c0_seq1   (736)  --------------------------------------------------
comp46218_c0_seq1 (809)  --------------------------------------------------
                          1651                                          1700
             ACS2 (1651) GACAAAACTAATGAGGTTTATAAGGTTGATGAGAGAGGCATGCGCTGGTT
comp167_c0_seq1   (736)  --------------------------------------------------
comp46218_c0_seq1 (809)  --------------------------------------------------
                          1701                                          1750
             ACS2 (1701) CTATACTGGTGACATTGGAAGGTTTCATCCCGATGGATGCATTGAAATTA
comp167_c0_seq1   (736)  --------------------------------------------------
comp46218_c0_seq1 (809)  --------------------------------------------------
                          1751                                          1800
             ACS2 (1751) TTGATAGAAAGAAAGATATCATTAAGCTTCAGCACGGGGAGTATATCTCA
comp167_c0_seq1   (736)  --------------------------------------------------
comp46218_c0_seq1 (809)  --------------------------------------------------
                          1801                                          1850
             ACS2 (1801) CTTGGAAAGGTTGAGGCAGCACTTTTATCAAGTGATTATGTGGAAAGCAT
comp167_c0_seq1   (736)  --------------------------------------------------
comp46218_c0_seq1 (809)  --------------------------------------------------
                          1851                                          1900
             ACS2 (1851) CATGGTCTACGCAGACCCTTTCCACAGTTATTGTGTAGCTTTAGTTGTCC
comp167_c0_seq1   (736)  --------------------------------------------------
comp46218_c0_seq1 (809)  --------------------------------------------------
                          1901                                          1950
             ACS2 (1901) CTTCACGCCAGGTGCTTGAGAAATGGTCCCAAGAAAATAGCATCCAGCAC
comp167_c0_seq1   (736)  --------------------------------------------------
comp46218_c0_seq1 (809)  --------------------------------------------------
                          1951                                          2000
             ACS2 (1951) AAAGATTTTTCTGAACTGTGTGACAAAGCAGAATCAGTCAATGAAATCAA
comp167_c0_seq1   (736)  --------------------------------------------------
comp46218_c0_seq1 (809)  --------------------------------------------------
                          2001                                          2050
             ACS2 (2001) GCAATCAATTTCAAAGGTAGCAAAAGCTGCAAGATTGGAAAAGTTTGAGC
comp167_c0_seq1   (736)  --------------------------------------------------
comp46218_c0_seq1 (809)  --------------------------------------------------
                          2051                                          2100
             ACS2 (2051) TTCCTGCCAAGATCAATTTAATACCAGAGTCTTGGACTCCCGAGACTGGA
comp167_c0_seq1   (736)  --------------------------------------------------
comp46218_c0_seq1 (809)  --------------------------------------------------
                          2101                                          2150
             ACS2 (2101) TTGGTAACTGCAGCTCTGAAATTGAAGCGGGAACCTCTGAAGGCTCGATA
comp167_c0_seq1   (736)  --------------------------------------------------
```

FIG. 4A (continued)

```
comp46218_c0_seq1   (809)  --------------------------------------------
                            2151                    2181
             ACS2  (2151)  TAAGAACGAGTTAGAAAAGTTGTATCAATGA
    comp167_c0_seq1 (736)  -------------------------------
 comp46218_c0_seq1  (809)  -------------------------------
```

FIG. 4A (continued)

```
                            1                                                50
             ACS2    (1)   ATGGAAGATTCTGAGGGAAGTAATCCATATACGAGTTCAGTGGAGAGACT
    comp167_c1_seq1  (1)   --------------------------------------------------
                            51                                               100
             ACS2   (51)   GACCAGCTATGATTATATCTCCAAAAATTATGGGTCATCTGGGGTTACTG
    comp167_c1_seq1  (1)   --------------------------------------------------
                            101                                              150
             ACS2  (101)   GTGCAGTTTTTATTGCCATTATTATGCCAATAATCCTCTCCATGTTACTT
    comp167_c1_seq1  (1)   --------------------------------------------------
                            151                                              200
             ACS2  (151)   ATGGGGAAGAAGAAGGCAAAACAGAGAGGTGTTCCGGTTCAAGTTGGTGG
    comp167_c1_seq1  (1)   --------------------------------------------------
                            201                                              250
             ACS2  (201)   TGAGGCAGGTCTTGCAATGCGCAATGTTAAATCAGCAAGATTAGTTGAAG
    comp167_c1_seq1  (1)   --------------------------------------------------
                            251                                              300
             ACS2  (251)   TTCCTTGGGAAGGGGCTACAACTGTACCAGCTCTATTTGAGCAGTCTTGC
    comp167_c1_seq1  (1)   --------------------------------------------------
                            301                                              350
             ACS2  (301)   AAAAAACATTCTTCTGATCGCTGTCTTGGAACTAGAAAACTAGTTAGCAG
    comp167_c1_seq1  (1)   --------------------------------------------------
                            351                                              400
             ACS2  (351)   GGACTTTGTTACTGCAAGTGATGGAAGGAAGTTTGAGAAACTTCACTTGG
    comp167_c1_seq1  (1)   --------------------------------------------------
                            401                                              450
             ACS2  (401)   GGGAGTATCAGTGGGAATCTTATGGACAAGTATTTGATCGCACTTGCAAC
    comp167_c1_seq1  (1)   --------------------------------------------------
                            451                                              500
             ACS2  (451)   TTTGCCTCTGGTCTTATTAAATTTGGTCATGATGTGGACACTCACGCTGC
    comp167_c1_seq1  (1)   --------------------------------------------------
                            501                                              550
             ACS2  (501)   TATCTGTGCAGAAACTCGTCCAGAGTGGATCATTGCCTTTCAGGGATGCT
    comp167_c1_seq1  (1)   --------------------------------------------------
                            551                                              600
             ACS2  (551)   TCCGGCAGAATATTACTGTTGTTACCATTTATGCTTCCTTGGGTGATGAT
    comp167_c1_seq1  (1)   --------------------------------------------------
                            601                                              650
             ACS2  (601)   GCACTCATTCATTCACTCAATGAGACCCAAGTATCTACATTGATATGTGA
    comp167_c1_seq1  (1)   --------------------------------------------------
                            651                                              700
             ACS2  (651)   TGCCAAGCAACTGAAAAAGTGGCTTCTGTTAGTTCGAGCCTGAAAACCA
    comp167_c1_seq1  (1)   --------------------------------------------------
                            701                                              750
             ACS2  (701)   TCAAGAATGTCATCTATTTTGAGGATGACGAGACGGCAATAGATTCCACA
    comp167_c1_seq1  (1)   --------------------------------------------------
                            751                                              800
             ACS2  (751)   AATATTGACAGCTGGAGGATGTCGTCTTTCTCAGCAGTTGAAAAGCTGGG
    comp167_c1_seq1  (1)   --------------------------------------------------
                            801                                              850
```

FIG. 4B

```
        ACS2   (801)  TAAAAATAGTCCTATTCAGCCAAGACTGCCTATCAAAGAAGATATTGCTG
comp167_c1_seq1  (1)  --------------------------------------------------
                      851                                              900
        ACS2   (851)  TGATCATGTATACAAGTGGCAGTACAGGCTTGCCTAAGGGTGTTATGATA
comp167_c1_seq1  (1)  --------------------------------------------------
                      901                                              950
        ACS2   (901)  ACTCATGGAAACATTGTAGCCACTTCAGCTGCTGTTATGACTGTGATTCC
comp167_c1_seq1  (1)  --------------------------------------------------
                      951                                             1000
        ACS2   (951)  GAACCTTGGAAGCAGTGATGTGTATTTGGCTTACCTTCCTTTAGCTCACG
comp167_c1_seq1  (1)  --------------------------------------------------
                      1001                                            1050
        ACS2  (1001)  TTTTTGAGCTAGCTGCCGAGACCGTAATGTTGACTGCAGGTGCTTGTATT
comp167_c1_seq1  (1)  --------------------------------------------------
                      1051                                            1100
        ACS2  (1051)  GGTTATGGCTCAGCTCTCACATTGACGGACACTTCTAACAAAGTCATGAA
comp167_c1_seq1  (1)  --------------------------------------------------
                      1101                                            1150
        ACS2  (1101)  GGGGACCAAGGGAGATGCTACAGTTTTAAAACCTACTTTAATGGCAGCAG
comp167_c1_seq1  (1)  --------------------------------------------------
                      1151                                            1200
        ACS2  (1151)  TTCCAGCCATTCTGGATCGTGTTCGGGATGGTGTTATGAAGAAGGTTGAG
comp167_c1_seq1  (1)  --------------------------------------------------
                      1201                                            1250
        ACS2  (1201)  GAGAAGGCAGGTTCTGCCAAGAAACTTTTCCACATTGGCTTTAACCGTCG
comp167_c1_seq1  (1)  --------------------------------------------------
                      1251                                            1300
        ACS2  (1251)  ATTGGCTGCTATGGAAGGTAGCTGGTTTGGAGCTTGGGGTCTAGAGAAAC
comp167_c1_seq1  (1)  --------------------------------------------------
                      1301                                            1350
        ACS2  (1301)  AATTGTGGGATATCATTATATTTAAAAAGGTGAGGGCTGTGCTTGGCGGA
comp167_c1_seq1  (1)  --------------------------------------------------
                      1351                                            1400
        ACS2  (1351)  GATATCCGTTTCATGCTTTGCGGTGGTGCTCCTCTATCAGGAGATACTCA
comp167_c1_seq1  (1)  --------------------------------------------------
                      1401                                            1450
        ACS2  (1401)  AAGATTTATCAACATTTGTATGGGAGCTCCTATTGGTCAAGGGTATGGCT
comp167_c1_seq1  (1)  --------------------------------------------------
                      1451                                            1500
        ACS2  (1451)  TGACAGAAACATTTGCTGGAGCTACTTTCTCTGAGTGGGATGATCCTTCT
comp167_c1_seq1  (1)  ------------------------------------------CTCGGGGA
                      1501                                            1550
        ACS2  (1501)  GTTGGGCGTGTTGGTCCACCTCTTCCTTGTTCCTACATAAAGCTTGTTAC
comp167_c1_seq1  (9)  GAAGTAGGTGTTGGTCCACCTCTTCCTTGTTCCTACATAAAGCTTGTTAC
                      1551                                            1600
        ACS2  (1551)  TTGGGAAGAAGGAGGTTACAGAATAGTTGATAAGCCTATGCCTCGGGGGG
comp167_c1_seq1 (59)  TTGGGAAGAAGGAGGTTACAGAATAGTTGATAAGCCTATGCCTCGGGGAG
                      1601                                            1650
        ACS2  (1601)  AAGTAGTTGTTGGTGGATGCAGCATCACTGCTGGTTACTTCAACAATGAG
comp167_c1_seq1(109)  AAGTAGTTGTTGGTGGATGCAGCATCACTGCTGGTTACTTCAACAATGAG
                      1651                                            1700
        ACS2  (1651)  GACAAAACTAATGAGGTTTATAAGGTTGATGAGAGAGGCATGCGCTGGTT
comp167_c1_seq1(159)  GACAAAACTAATGAGGTTTATAAGGTTGATGAGAGAGGCATGCGCTGGTT
                      1701                                            1750
        ACS2  (1701)  CTATACTGGTGACATTGGAAGGTTTCATCCCGATGGATGCATTGAAATTA
comp167_c1_seq1(209)  CTATACTGGTGACATTGGAAGGTTTCATCCCGATGGATGCATTGAAATTA
                      1751                                            1800
```

FIG. 4B (continued)

```
        ACS2  (1751)  TTGATAGAAAGAAAGATATCATTAAGCTTCAGCACGGGGAGTATATCTCA
comp167_c1_seq1 (259) TTGATAGAAAGAAAGATATCGTTAAGCTTCAGCACGGGGAGTATATCTCA
                     1801                                             1850
        ACS2  (1801)  CTTGGAAAGGTTGAGGCAGCACTTTTATCAAGTGATTATGTGGAAAGCAT
comp167_c1_seq1 (309) CTTGGAAAGGTTGAGGCAGCACTTTTATCAAGTGATTATGTGGAAAGCAT
                     1851                                             1900
        ACS2  (1851)  CATGGTCTACGCAGACCCTTTCCACAGTTATTGTGTAGCTTTAGTTGTCC
comp167_c1_seq1 (359) CATGGTCTACGCGGACCCCTTCCACAATTATTGTGTAGCTTTAATTGTCC
                     1901                                             1950
        ACS2  (1901)  CTTCACGCCAGGTGCTTGAGAAATGGTCCCAAGAAAATAGCATCCAGCAC
comp167_c1_seq1 (409) CTTCACGCCAGGTGCTTGAGAAATGGTCCC--------------------
                     1951                                             2000
        ACS2  (1951)  AAAGATTTTTCTGAACTGTGTGACAAAGCAGAATCAGTCAATGAAATCAA
comp167_c1_seq1 (439) --------------------------------------------------
                     2001                                             2050
        ACS2  (2001)  GCAATCAATTTCAAAGGTAGCAAAAGCTGCAAGATTGGAAAAGTTTGAGC
comp167_c1_seq1 (439) --------------------------------------------------
                     2051                                             2100
        ACS2  (2051)  TTCCTGCCAAGATCAATTTAATACCAGAGTCTTGGACTCCCGAGACTGGA
comp167_c1_seq1 (439) --------------------------------------------------
                     2101                                             2150
        ACS2  (2101)  TTGGTAACTGCAGCTCTGAAATTGAAGCGGGAACCTCTGAAGGCTCGATA
comp167_c1_seq1 (439) --------------------------------------------------
                     2151                2181
        ACS2  (2151)  TAAGAACGAGTTAGAAAAGTTGTATCAATGA
comp167_c1_seq1 (439) -------------------------------
```

FIG. 4B (continued)

|            |       | 1                                                    50 |
|------------|-------|----------------------------------------------------------|
| ACS1       | (1)   | MATDKFIIEVESAKPAKDGRPSMGPVYRSIFAKHGFPPPIPGLDSCWDIF |
| Ghost ACS1 | (1)   | MATDKFIIEVESAKPAKDGRPSMGPVYRSIFAKHGFPPPIPGLDSCWDIF |
|            |       | 51                                                  100 |
| ACS1       | (51)  | RMSVEKYPNNRMLGRREIVDGKPGKYVWMSYKEVYDIVIKVGNSIRSIGV |
| Ghost ACS1 | (51)  | RMSVEKYPNNRMLGRREIVDGKPGKYVWMSYKEVYDIVIKVGNSIRSIGV |
|            |       | 101                                                 150 |
| ACS1       | (101) | DVGDKCGIYGANCPEWIISMEACNAHGLYCVPLYDTLGAGAVEFIISHAE |
| Ghost ACS1 | (101) | DVGDKCGIYGANCPEWIISMEACNAHGLYCVPLYDTLGAGAVEFIISHAE |
|            |       | 151                                                 200 |
| ACS1       | (151) | VTIAFVEEKKLPELLKTFPNASKYLKTIVSFGKVTPEQKKELEEFGVVLY |
| Ghost ACS1 | (151) | VTIAFVEEKKLPELLKTFPNASKYLKTIVSFGKVTPEQKKELEEFGVVLY |
|            |       | 201                                                 250 |
| ACS1       | (201) | SWDEFLQLGSGKQFDLPVKKKEDICTIMYTSGTTGDPKGVLISNTSIVTL |
| Ghost ACS1 | (201) | SWDEFLQLGSGKQFDLPVKKKEDICTIMYTSGTTGDPKGVLISNTSIVTL |
|            |       | 251                                                 300 |
| ACS1       | (251) | IAGVRRFLGSVDESLNVDDVYLSYLPLAHIFDRVIEECFIHHGASIGFWR |
| Ghost ACS1 | (251) | IAGVRRFLGSVDESLNVDDVYLSYLPLAHIFDRVIEECFIHHGASIGFWR |
|            |       | 301                                                 350 |
| ACS1       | (301) | GDVKLLTEDIGELKPTVFCAVPRVLDRIYSGLQQKIAAGGFLKSTLFNLA |
| Ghost ACS1 | (301) | GDVKLLTEDIGELKPTVFCAVPRVLDRIYSGLQQKIAAGGFLKSTLFNLA |
|            |       | 351                                                 400 |
| ACS1       | (351) | YAYKHHNLKKGRKHFEASPLSDKVVFSKVKEGLGGRVRLILSGAAPLAAH |
| Ghost ACS1 | (351) | YAYKHHNLKKGRKHFEASPLSDKVVFSKVKEGLGGRVRLILSGAAPLAAH |
|            |       | 401                                                 450 |
| ACS1       | (401) | VEAFLRVVACCHVLQGYGLTETCAGTFVSLPNRYDMLGTVGPPVPNVDVC |
| Ghost ACS1 | (401) | VEAFLRVVACCHVLQGYGLTETCAGTFVSLPNRYDMLGTVGPPVPNVDVC |
|            |       | 451                                                 500 |
| ACS1       | (451) | LESVPEMSYDALSSTPRGEVCVRGDILFSGYYKREDLTKEVMIDGWFHTG |
| Ghost ACS1 | (451) | LESVPEMSYDALSSTPRGEVCVRGD<u>V</u>LFSGYYKREDLTKEVMIDGWFHTG |
|            |       | 501                                                 550 |
| ACS1       | (501) | DVGEWQPNGSLKIIDRKKNIFKLSQGEYVAVENLENIYGNNPIIDSIWIY |
| Ghost ACS1 | (501) | DVGEWQPNGSLKIIDRKKNIFKLSQGEYVAVENLENIYGNNPIIDSIWIY |
|            |       | 551                                                 600 |
| ACS1       | (551) | GNSFESFLVAVINPNQRAVEQWAEVNGLSGDFASLCEKPEVKEYILRELT |
| Ghost ACS1 | (551) | GNSFESFLVAVINPNQRAVEQWAEVNGLSGDFASLCEKPEVKEYILRELT |
|            |       | 601                                                 650 |
| ACS1       | (601) | KTGKEKKLKGFEFLKAVHLDPVPFDMERDLLTPTFKKKRPQLLKYYKDVI |
| Ghost ACS1 | (601) | KTGKEKKLKGFEFLKAVHLDPVPFDMERDLLTPTFKKKRPQLLKYYKDVI |
|            |       | 651 |
| ACS1       | (651) | DSMYKGTK |
| Ghost ACS1 | (651) | DSMYKGTK |

FIG. 5

```
               1                                                  50
AtLACS4    (1) MSQQKKYIFQVEEGKEGSDGRPSVGPVYRSIFAKDGFPDPIEGMDSCWDV
AtLCAS5    (1) MTSQKRFIFEVEAAKEATDGNPSVGPVYRSTFAQNGFPNPIDGIQSCWDI
Ghost ACS1 (1) -MATDKFIIEVESAKPAKDGRPSMGPVYRSIFAKHGFPPPIPGLDSCWDI
               51                                                100
AtLACS4   (51) FRMSVEKYPNNPMLGRREIVDGKPGKYVWQTYQEVYDIVMKLGNSLRSVG
AtLCAS5   (51) FRTAVEKYPNNRMLGRREISNGKAGKYVWKTYKEVYDIVIKLGNSLRSCG
Ghost ACS1 (50) FRMSVEKYPNNRMLGRREIVDGKPGKYVWMSYKEVYDIVIKVGNSIRSIG
               101                                               150
AtLACS4  (101) VKDEAKCGIYGANSPEWIISMEACNAHGLYCVPLYDTLGADAVEFIISHS
AtLCAS5  (101) IKEGEKCGIYGINCCEWIISMEACNAHGLYCVPLYDTLGAGAVEFIISHA
Ghost ACS1(100) VDVGDKCGIYGANCPEWIISMEACNAHGLYCVPLYDTLGAGAVEFIISHA
               151                                               200
AtLACS4  (151) EVSIVFVEEKKISELFKTCPNSTEYMKTVVSFGGVSREQKEEAETFGLVI
AtLCAS5  (151) EVSIAFVEEKKIPELFKTCPNSTKYMKTVVSFGGVKPEQKEEAEKLGLVI
Ghost ACS1(150) EVTIAFVEEKKLPELLKTFPNASKYLKTIVSFGKVTPEQKKELEEFGVVL
               201                                               250
AtLACS4  (201) YAWDEFLKLGEGKQYDLPIKKKSDICTIMYTSGTTGDPKGVMISNESIVT
AtLCAS5  (201) HSWDEFLKLGEGKQYELPIKKPSDICTIMYTSGTTGDPKGVMISNESIVT
Ghost ACS1(200) YSWDEFLQLGSGKQFDLPVKKKEDICTIMYTSGTTGDPKGVLISNTSIVT
               251                                               300
AtLACS4  (251) LIAGVIRLLKSANEALTVKDVYLSYLPLAHIFDRVIEECFIQHGAAIGFW
AtLCAS5  (251) ITTGVMHFLGNVNASLSEKDVYISYLPLAHVFDRAIEECIIQVGGSIGFW
Ghost ACS1(250) LIAGVRRFLGSVDESLNVDDVYLSYLPLAHIFDRVIEECFIHHGASIGFW
               301                                               350
AtLACS4  (301) RGDVKLLIEDLAELKPTIFCAVPRVLDRVYSGLQKKLSDGGFLKKFIFDS
AtLCAS5  (301) RGDVKLLIEDLGELKPSIFCAVPRVLDRVYTGLQQKLSGGGFFKKKVFDV
Ghost ACS1(300) RGDVKLLTEDIGELKPTVFCAVPRVLDRIYSGLQQKIAAGGFLKSTLFNL
               351                                               400
AtLACS4  (351) AFSYKFGYMKKGQSHVEASPLFDKLVFSKVKQGLGGNVRIILSGAAPLAS
AtLCAS5  (351) AFSYKFGNMKKGQSHVAASPFCDKLVFNKVKQGLGGNVRIILSGAAPLAS
Ghost ACS1(350) AYAYKHHNLKKGRKHFEASPLSDKVVFSKVKEGLGGRVRLILSGAAPLAA
               401                                               450
AtLACS4  (401) HVESFLRVVACCHVLQGYGLTESCAGTFVSLPDELGMLGTVGPPVPNVDI
AtLCAS5  (401) HIESFLRVVACCNVLQGYGLTESCAGTFATFPDELDMLGTVGPPVPNVDI
Ghost ACS1(400) HVEAFLRVVACCHVLQGYGLTETCAGTFVSLPNRYDMLGTVGPPVPNVDV
               451                                               500
AtLACS4  (451) RLESVPEMEYDALASTARGEICIRGKTLFSGYYKREDLTKEVLIDGWLHT
AtLCAS5  (451) RLESVPEMNYDALGSTPRGEICIRGKTLFSGYYKREDLTKEVFIDGWLHT
Ghost ACS1(450) CLESVPEMSYDALSSTPRGEVCVRGDVLFSGYYKREDLTKEVMIDGWFHT
               501                                               550
AtLACS4  (501) GDVGEWQPDGSMKIIDRKKNIFKLSQGEYVAVENIENIYGEVQAVDSVWV
AtLCAS5  (501) GDVGEWQPNGSMKIIDRKKNIFKLAQGEYVAVENLENVYSQVEVIESIWV
Ghost ACS1(500) GDVGEWQPNGSLKIIDRKKNIFKLSQGEYVAVENLENIYGNNPIIDSIWI
               551                                               600
AtLACS4  (551) YGNSFESFLIAIANPNQHILERWAAENGVSGDYDALCQNEKAKEFILGEL
AtLCAS5  (551) YGNSFESFLVAIANPAQQTLERWAVENGVNGDFNSICQNAKAKAFILGEL
Ghost ACS1(550) YGNSFESFLVAVINPNQRAVEQWAEVNGLSGDFASLCEKPEVKEYILREL
               601                                               650
AtLACS4  (601) VKMAKEKKMKGFEIIKAIHLDPVPFDMERDLLTPTFKKKRPQLLKYYQSV
AtLCAS5  (601) VKTAKENKLKGFEIIKDVHLEPVAFDMERDLLTPTYKKKRPQLLKYYQNV
Ghost ACS1(600) TKTGKEKKLKGFEFLKAVHLDPVPFDMERDLLTPTFKKKRPQLLKYYKDV
               651       666
AtLACS4  (651) IDEMYKTINAKFASRG
AtLCAS5  (651) IHEMYKTTKETLASGQ
Ghost ACS1(650) IDSMYKGTK-------
```

FIG. 6

S1-1 sample Full MS scan
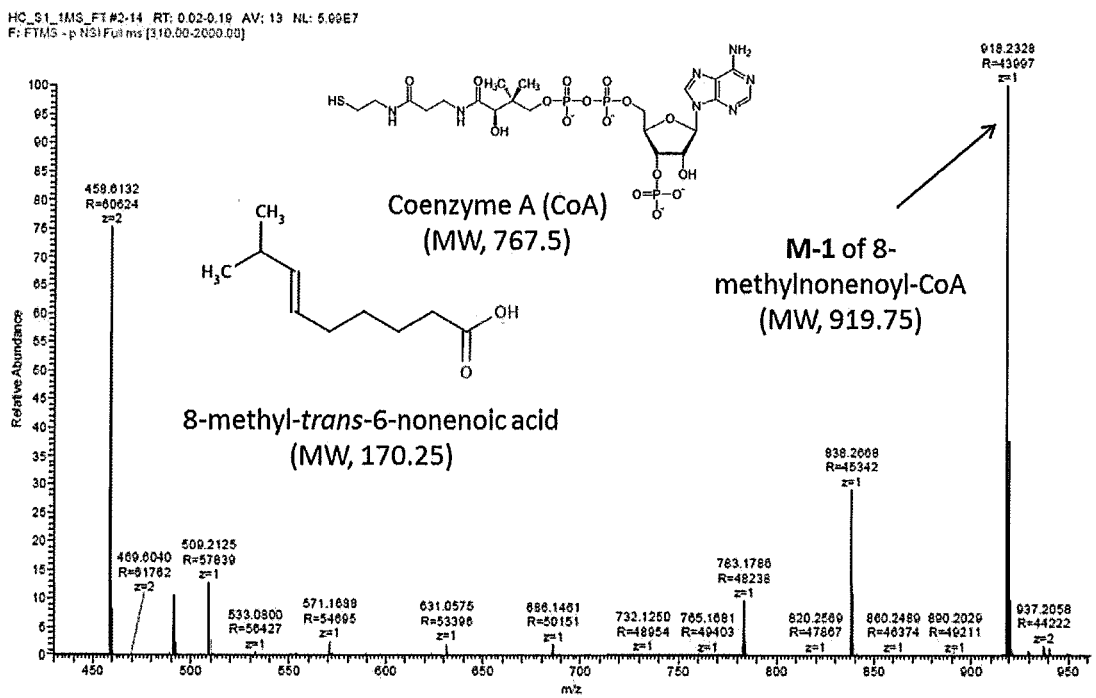
S1-1 sample MS2 scan
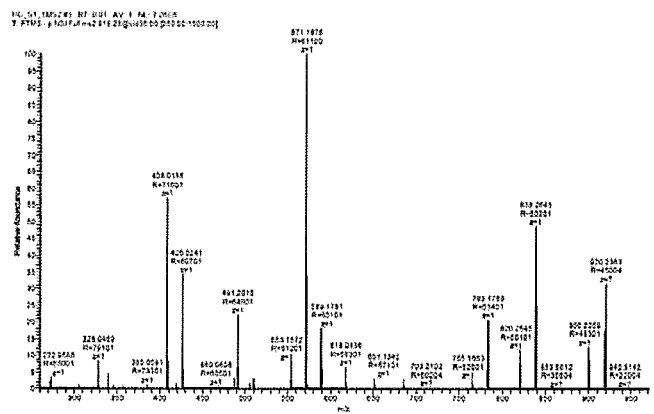
FIG. 10

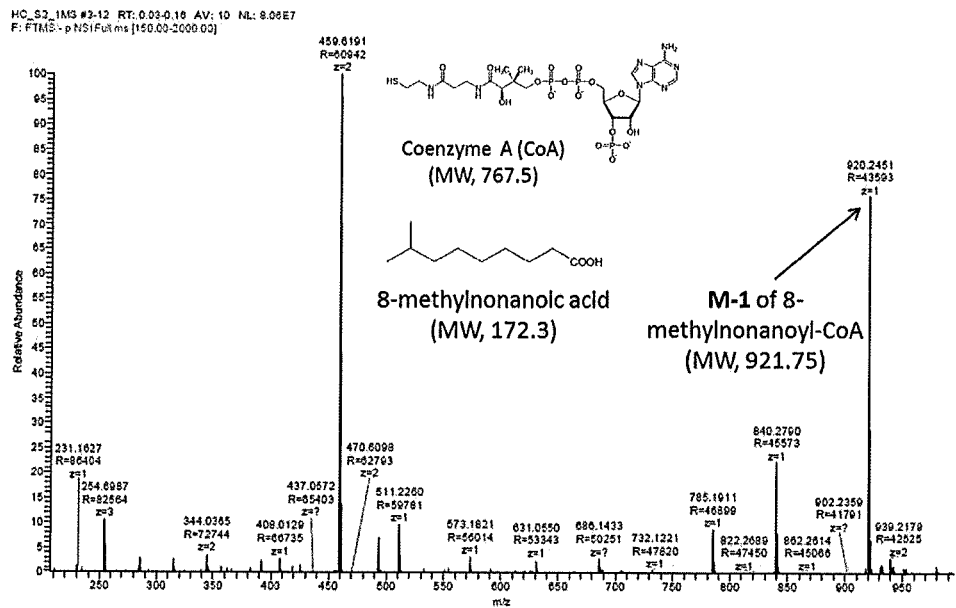
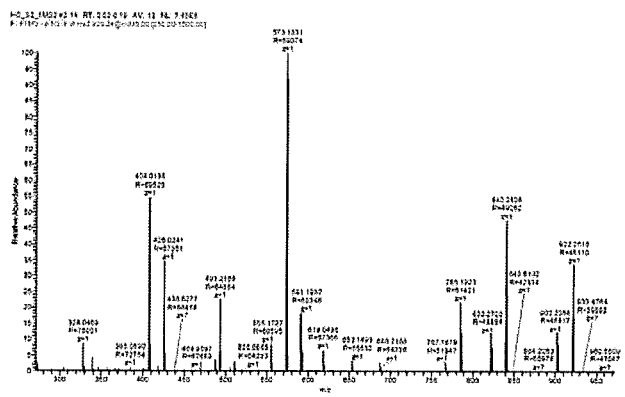
FIG. 11

SEQUENCE LISTING

<160> NUMBER OF SEQ ID NOS: 15

<210> SEQ ID NO 1
<211> LENGTH: 40
<212> TYPE: DNA

```
<213> ORGANISM: Artificial Sequence
<220> FEATURE:
<223> OTHER INFORMATION: Primer

<400> SEQUENCE: 1
cgcgaacaga ttggaggtgc aacagataaa tttattattg                            40

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
gtggcggccg ctctattatc acttggtacc cttgtacat                             39

<210> SEQ ID NO 3
<211> LENGTH: 1900
<212> TYPE: DNA
<213> ORGANISM: Capsicum annuum

<400> SEQUENCE: 3
gtgggtattg aatctcttat tcttcgccta tggagtgttt gacgctaact ggattcttga      60
aacatgtggc tgaaaagtac cctagtcatc gtgcgatttc cgtttccggc aggctcgata    120
tcactcatgc acgccttcaa caactcgttg aacgtgccgc ttctcagatt gtagctgccg    180
gtgtaaagcc tggcgatgtc gtcgctctca ctttccccaa cacaatcgag ttcgtgatca    240
tgtttttagc tgtaattcga gctcgagcta cagcagcgcc actgaattca gcgtacatgg    300
cagaagaatt cgagttttat ttatctgatt cagaatcgaa actcttatta actgcaaaag    360
aaggaaacga agcagctcaa gctgctgcct ccaagctaaa aatccctcgt attagtgtaa    420
ctctctctca acccgactct gatgtcgctt tctccccagc tccacccgaa tcggaccttg    480
aatcgatgtc caaaatcgtt aacgaaccat cagatgttgg acttttcctt catacatcag    540
gcaccactag caggccaaaa ggtgttcctc tggctcagct gaatttgttg tcttcagtaa    600
acaatatcaa atcggtgtac aaaactgagtg acacggattc tactgtgatt gtgttgccgt    660
tgtttcacgt tcacgggtta attgcggggt tactgagctc acttggagcc ggagcagccg    720
tgacacttcc agctgcaggg agattttcag cttcgacttt ttggtcagac atgaaaaaat    780
acaacgcaac atggtacaca gctgtgccta ctattcacca aattctattg gatcgtcacc    840
tcagcaaacc cgaatcggat tacccaaagc ttcggttcat tcggagctgt agtgcagcac    900
tggctccatc agtgatggcg cggctagaag aagcattcgc ggctcctgtt ttggaggcgt    960
atgcaatgac tgaggcaacc catttgatgg cttcgaaccc cttacccgag gatggcccac   1020
atattcccgg gtcagttggg aaacccgtgg gtcaagagat gggcattttg aatgagaatg   1080
gggagttaca agggcctaat gctaaagggg aagtttgtat aagggtcca aatgtgacaa   1140 agggatacaa gaacaatcca gaggcaaata atcagctttt ccagtttggt tggttttcaca   1200 ctggagatgt ggggtatttg gactctgatg gatacttgca tttggttgga agaatcaagg   1260
agttgatcaa ccgcggaggg gagaaaatat cacctattga attggatgca gtcctagttt   1320
ctcatccaga aattgctcag gctgttgctt ttggagtccc tgacgacaag tatggtgaag   1380
agataaactg tgcagttatt ccaagagaag ggtcaaacat cgatgaagca gaggtgctga   1440
gattttgcaa gaagaatttg gcagccttta aggtcccaaa gaaggtcttc atgactgatt   1500
ctcttccaaa aactgcatca ggaaaaattc aacgccgact cgttgcagag cacttccttg   1560
```

-continued

| | |
|---|---|
| cacagatttc aactgctaaa gtccccaagt ttggagcata gaaaaattgt tggctatcta | 1620 |
| cgattccttc tcctattaac aataataaaa atgtgctttt cgatattact tacgtaccat | 1680 |
| actacttggt caagaaatcg ggacacgaga atatatcagt gcctctagat tttcagtaat | 1740 |
| ggcgcaagta tattctctta tagtcttttc agggtagata ttttgtattt ctctacttag | 1800 |
| tattgcaaag gttctttat ttgtaagttg tgacaatgcc ttggacaaat gaatgaaagt | 1860 |
| gcagtttgta aggcccttat ttaaaaaaaa aaaaaaaaaa | 1900 |

<210> SEQ ID NO 4
<211> LENGTH: 1572
<212> TYPE: DNA
<213> ORGANISM: Ghost Chili Pepper

<400> SEQUENCE: 4

| | |
|---|---|
| atggagtgtt tgacgctaac tggattcttg aaacatgtgg ctgaaaagta ccctagtcat | 60 |
| cgtgcgattt ccgtttccgg caggctcgat atcactcatg cacgccttca acaactcgtt | 120 |
| gaacgtgccg cttctcagat tgtagctgcc ggtgtaaagc ctggcgatgt cgtcgctctc | 180 |
| actttcccca acacaatcga gttcgtgatc atgtttttag ctgtaattcg agctcgagct | 240 |
| acagcagcgc cactgaattc agcgtacatg gcagaagaat tcgagtttta tttatctgat | 300 |
| tcagaatcga aactcttatt aactgcaaaa gaaggaaacg aagcagctca agctgctgcc | 360 |
| tccaagctaa aaatccctcg tattagtgta actctctctc aacccgactc tgatgtcgct | 420 |
| ttctcccctg ctccacccga atcggacctt gaatcgatgt ccaaaatcgt taacgaacca | 480 |
| tcagatgttg acttttcct tcatacatca ggcaccacta gcaggccaaa aggtgttcct | 540 |
| ctgtctcagc tgaatttgtt gtcttcagta agcaatatca atcggtgta caaactgagt | 600 |
| gacacggatt ctactgtgat tgtgttgccg ttgtttcacg ttcacgggtt aattgcgggg | 660 |
| ttactgagct cacttggagc cggagcagcc gtgacacttc cagctgcagg gagattttca | 720 |
| gcttcgactt tttggtcaga catgaaaaaa tacaacgcaa catggtacac agctgtgcct | 780 |
| acaattcacc aaattctatt ggatcgtcac ctcagcaaac ccgaatcgga ttacccaaag | 840 |
| cttcggttca ttcggagctg tagtgcagca ctggctccat cagtgatggc gcggctggaa | 900 |
| gaagcattcg gggctcctgt tttggaggcg tatgcaatga ctgaggcaac ccatttgatg | 960 |
| gcttcgaacc ccttacccga ggatggccca catattcccg ggtcagttgg gaaacccgtg | 1020 |
| ggtcaagaga tgggcatttt gaatgagaat ggggagttac aagggcctaa tgctaaaggg | 1080 |
| gaagtttgta taaggggtcc aaatgtgaca aagggataca agaacaatcc agaggcaaat | 1140 |
| aaatcagctt tccagtttgg ttggtttcac actggagatg tggggtattt ggactctgat | 1200 |
| ggatacttgc atttggttgg aagaatcaag gagttgatca accgcggagg ggagaaaata | 1260 |
| tcacctattg aattggatgc agtcctagtt tctcatccag aaattgctca ggctgttgct | 1320 |
| tttgagtcc ctgacgacaa gtatggtgaa gagataaact gtgcagttat tccaagagaa | 1380 |
| gggtcaaaca tcgatgaagc agaggtgctg agattttgca agaagaattt ggcagccttt | 1440 |
| aaggtcccaa agaaggtctt catgactgat tctcttccaa aaactgcatc aggaaaaatt | 1500 |
| caacgccgac tcgttgcaga gcacttcctt gcacagattt caactgctaa agtccccaag | 1560 |
| tttggagcat ag | 1572 |

<210> SEQ ID NO 5
<211> LENGTH: 1977
<212> TYPE: DNA

<213> ORGANISM: Capsicum annuum

<400> SEQUENCE: 5

```
atggcaacag ataaatttat tattgaagtt gaatcagcaa aacctgctaa agatggaaga      60
ccatcaatgg gtcctgttta tagaagtatt tttgctaaac atggatttcc tccacctatt     120
cctgggcttg atagttgctg ggatattttt cgtatgtcag tggagaaata tcctaacaat     180
cggatgcttg gacgccgtga gattgtagat ggaaaacctg gcaagtatgt gtggatgtct     240
tacaaagaag tttatgacat tgtgattaaa gtaggaaatt ccatccggag cattggtgtg     300
gatgtgggag acaaatgtgg tatctatggt gccaattgcc ctgagtggat aataagcatg     360
gaggcatgca atgctcatgg actttactgt gttcctctgt atgacacctt aggtgctggt     420
gctgtggaat ttatcatttc ccatgctgag gttacaattg cttttgttga agagaaaaaa     480
cttcctgagc ttctgaaaac ttttccaaat gcgtcaaagt acttgaaaac tattgtgagt     540
ttcggaaagg tcactcctga acagaaaaaa gagcttgaag agtttgggt ggttctttac      600
tcgtgggatg agtttcttca attgggaagc ggaaaacaat ttgatcttcc agtgaaaaag     660
aaggaagaca tctgtacaat aatgtatact agtggaacga ccggagaccc caaaggtgtc     720
ctgatttcaa atactagcat tgttactctt atagctggag taaggcgttt ccttgggagc     780
gtggatgagt cgttgaatgt ggacgatgtg tatctttcgt atcttcccct ggcacatatc     840
tttgatcgag tgattgaaga gtgtttcatt catcatggtg cctcgatagg attttggcga     900
ggggatgtca agttactaac cgaagatatt ggagaactga accaactgt cttctgtgct       960
gtacctcggg tactagacag aatatattca ggtttgcaac agaaaattgc tgctggtggt    1020
tttctcaaaa gcacgttgtt caatcttgcc tatgcttaca acaccacaa tttgaagaag     1080
gggcgtaaac actttgaagc ttctccgctt tctgacaaag ttgtcttcag taaggtaaaa    1140
gaagggttag gaggcagagt acgacttata ttgtctggag cagcgcccct tgcagctcat    1200
gtggaagctt ttttgcgagt gtggcatgc tgtcacgttc ttcaaggata tggttttgact    1260
gaaacgtgtg ctggtacatt tgtgtcgcta cccaaccggt atgatatgct tggtacggtt    1320
ggtcctcccg tgcccaacgt ggatgtgtgc ttggagtccg ttcctgaaat gtcatatgat    1380
gctttgtcaa gcacgccacg tggagaagtg tgtgtgaggg gggacattct attttcaggc    1440
tattacaagc gtgaggacct aacgaaagaa gtcatgattg atgggtggtt tcacacaggt    1500
gatgttggcg agtggcaacc taacggtagc ttgaaaataa ttgaccgcaa gaagaacatt    1560
ttcaagctct cacaaggtga atatgtggct gtcgaaaatc tggagaatat ctatggcaat    1620
aatcctatta ttgactcgat atggatatac gggaacagtt tcgagtcctt ccttgttgct    1680
gttattaacc caaaccaacg agcagttgaa caatgggccg aagttaatgg cttgtctggg    1740
gattttgctt ccttgtgtga aaagccggaa gtgaaagagt acatacttcg agagctaaca    1800
aaaaccggaa agaaaagaa gttgaagggc tttgagttcc taaaagcggt acaccttgat    1860
cctgtgccat tcgacatgga acgagacctt ctaactccga cattcaagaa gaaaagaccc    1920
caattgctca aatactacaa ggatgtgatt gacagcatgt acaagggtac caagtga       1977
```

<210> SEQ ID NO 6
<211> LENGTH: 1515
<212> TYPE: DNA
<213> ORGANISM: Ghost Chili Pepper

<400> SEQUENCE: 6

```
atggcaacag ataaatttat tattgaagtt gaatcagcaa aacctgctaa agatggaaga      60
```

-continued

```
ccatcaatgg gtcctgttta tagaagtatt tttgctaaac atggattcc tccacctatt      120 cctgggcttg atagttgctg ggatatttt cgtatgtcag tggagaaata tcctaacaat      180
cggatgcttg gacgccgtga gattgtagat ggaaaacctg gcaagtatgt gtggatgtct     240
tacaaagaag tttatgacat tgtgattaaa gtaggaaatt ccatccggag cattggtgtg     300
gatgtgggag acaaatgtgg tatctatggt gccaattgcc ctgagtggat aataagcatg     360
gaggcatgca atgctcatgg actttactgt gttcctctgt atgacacctt aggtgctggt     420
gctgtggaat ttatcatttc ccatgctgag gttacaattg cttttgttga agagaaaaaa     480
cttcctgagc ttctgaaaac ttttccaaat gcgtcaaagt acttgaaaac tattgtgagt     540
ttcggaaagg tcactcctga acagaaaaaa gagcttgaag agtttggggt ggttcttttac    600 tcgtgggatg agtttcttca attgggaagc ggaaaacaat ttgatcttcc agtgaaaaag     660
aaggaagaca tctgtacaat aatgtatact agtggaacga ccggagaccc caaaggtgtc    720
ctgatttcaa atactagcat tgttactctt atagctggga taaggcgttt ccttgggagc    780
gtggatgagt cgttgaatgt ggacgatgtg tatctttcgt atcttcccct ggcacatatc    840
tttgatcgag tgattgaaga gtgtttcatt catcatggtg cctcgatagg attctggcga    900
ggggatgtca agttactaac cgaagatatt ggagaactga aaccaaccgt cttctgtgct    960
gtacctcggg tactagacag aatatattca ggtttgcaac agaaaattgc tgctggtggt   1020
tttctcaaaa gcacgttgtt caatcttgcc tatgcttaca acaccacaa tttgaagaag    1080 gggcgtaaac actttgaagc ttctccgctt tctgacaaag ttgtcttcag taaggtaaaa   1140
gaagggttag gaggcagagt acgacttata ttgtctggag cagcgcccct tgcagctcat   1200
gtggaagctt ttttgcgagt tgtggcatgc tgtcacgttc ttcaaggata tggtttgact   1260
gaaacgtgtg ctggtacatt tgtgtcgcta cccaaccggt atgatatgct tggtacggtt   1320
ggtcctcccg tgcccaacgt ggatgtgtgc ttggagtccg ttcctgaaat gtcatatgat   1380
gctttgtcaa gcacgccacg tggagaagtg tgtgtgaggg gggacgttct attttcaggc   1440
tattacaagc gtgaggacct aacaaaagaa gtcatgattg atgggtggtt tcacacaggt   1500
gatgttggcg agtgg                                                    1515

<210> SEQ ID NO 7
<211> LENGTH: 445
<212> TYPE: DNA
<213> ORGANISM: Ghost Chili Pepper

<400> SEQUENCE: 7
cacaggtgat gttggcgagt ggcaacctaa cggtagcttg aaaataattg accgcaagaa      60
gaacattttc aagctctcac aaggtgaata tgttgctgtc gaaatctgg agaatatcta     120 tggcaataat cctattattg actcgatatg gatatacggg aacagtttcg agtccttcct    180
tgttgctgtt attaacccaa accaacgagc agttgaacaa tgggccgaag ttaatggctt    240 gtctggggt tttgcttcct tgtgtgaaaa gccggaagtg aaagagtaca tacttcgaga     300
gctaacaaaa accggaaaag aaaagaagtt gaagggcttt gagttcctaa aagcggtaca    360
ccttgatcct gtgccattcg acatggaacg agaccttcta actccgacat tcaagaagaa    420
aagaccccaa ttgctcaaat actac                                         445

<210> SEQ ID NO 8
<211> LENGTH: 2181
<212> TYPE: DNA
```

<213> ORGANISM: Capsicum annuum

<400> SEQUENCE: 8

| | | | | | | |
|---|---|---|---|---|---|---|
| atggaagatt | ctgagggaag | taatccatat | acgagttcag | tggagagact | gaccagctat | 60 |
| gattatatct | ccaaaaatta | tgggtcatct | ggggttactg | gtgcagtttt | tattgccatt | 120 |
| attatgccaa | taatcctctc | catgttactt | atggggaaga | agaaggcaaa | acagagaggt | 180 |
| gttccggttc | aagttggtgg | tgaggcaggt | cttgcaatgc | gcaatgttaa | atcagcaaga | 240 |
| ttagttgaag | ttccttggga | agggctaca | actgtaccag | ctctatttga | gcagtcttgc | 300 |
| aaaaaacatt | cttctgatcg | ctgtcttgga | actagaaaac | tagttagcag | ggactttgtt | 360 |
| actgcaagtg | atggaaggaa | gtttgagaaa | cttcacttgg | gggagtatca | gtgggaatct | 420 |
| tatggacaag | tatttgatcg | cacttgcaac | tttgcctctg | gtcttattaa | atttggtcat | 480 |
| gatgtggaca | ctcacgctgc | tatctgtgca | gaaactcgtc | cagagtggat | cattgccttt | 540 |
| cagggatgct | tccggcagaa | tattactgtt | gttaccattt | atgcttcctt | gggtgatgat | 600 |
| gcactcattc | attcactcaa | tgagacccaa | gtatctacat | tgatatgtga | tgccaagcaa | 660 |
| ctgaaaaaag | tggcttctgt | tagttcgagc | ctgaaaacca | tcaagaatgt | catctatttt | 720 |
| gaggatgacg | agacggcaat | agattccaca | aatattgaca | gctggaggat | gtcgtctttc | 780 |
| tcagcagttg | aaaagctggg | taaaaatagt | cctattcagc | caagactgcc | tatcaaagaa | 840 |
| gatattgctg | tgatcatgta | tacaagtggc | agtacaggct | gcctaaggg | tgttatgata | 900 |
| actcatggaa | acattgtagc | cacttcagct | gctgttatga | ctgtgattcc | gaaccttgga | 960 |
| agcagtgatg | tgtatttggc | ttaccttcct | ttagctcacg | tttttgagct | agctgccgag | 1020 |
| accgtaatgt | tgactgcagg | tgcttgtatt | ggttatggct | cagctctcac | attgacggac | 1080 |
| acttctaaca | aagtcatgaa | ggggaccaag | ggagatgcta | cagtttttaaa | acctacttta | 1140 |
| atggcagcag | ttccagccat | tctggatcgt | gttcgggatg | tgttatgaa | gaaggttgag | 1200 |
| gagaaggcag | gttctgccaa | gaaacttttc | cacattggct | taaccgtcg | attggctgct | 1260 |
| atggaaggta | gctggtttgg | agcttggggt | ctagagaaac | aattgtggga | tatcattata | 1320 |
| tttaaaaagg | tgagggctgt | gcttggcgga | gatatccgtt | tcatgctttg | cggtggtgct | 1380 |
| cctctatcag | gagatactca | aagatttatc | aacatttgta | tgggagctcc | tattggtcaa | 1440 |
| gggtatggct | tgacagaaac | atttgctgga | gctactttct | ctgagtggga | tgatccttct | 1500 |
| gttgggcgtg | ttggtccacc | tcttccttgt | tcctacataa | agcttgttac | ttgggaagaa | 1560 |
| ggaggttaca | gaatagttga | taagcctatg | cctcgggggg | aagtagttgt | tggtggatgc | 1620 |
| agcatcactg | ctggttactt | caacaatgag | gacaaaacta | atgaggttta | taaggttgat | 1680 |
| gagagaggca | tgcgctggtt | ctatactggt | gacattggaa | ggtttcatcc | cgatggatgc | 1740 |
| attgaaatta | ttgatagaaa | gaaagatatc | attaagcttc | agcacgggga | gtatatctca | 1800 |
| cttgaaaagg | ttgaggcagc | acttttatca | agtgattatg | tggaaagcat | catggtctac | 1860 |
| gcagacccctt | tccacagtta | ttgtgtagct | ttagttgtcc | cttcacgcca | ggtgcttgag | 1920 |
| aaatggtccc | aagaaaatag | catccagcac | aaagattttt | ctgaactgtg | tgacaaagca | 1980 |
| gaatcagtca | atgaaatcaa | gcaatcaatt | tcaaaggtag | caaaagctgc | aagattggaa | 2040 |
| aagtttgagc | ttcctgccaa | gatcaattta | ataccagagt | cttggactcc | cgagactgga | 2100 |
| ttggtaactg | cagctctgaa | attgaagcgg | gaacctctga | aggctcgata | taagaacgag | 2160 |
| ttagaaaagt | tgtatcaatg | a | | | | 2181 |

<210> SEQ ID NO 9
<211> LENGTH: 735
<212> TYPE: DNA
<213> ORGANISM: Ghost Chili Pepper

<400> SEQUENCE: 9

```
agctgggtaa aaatagtcct attcggccaa gactgcctat caaagaagat attgctgtga    60
tcatgtatac aagtggcagt acaggcttgc ctaagggtgt tatgataact catggaaaca   120
ttgtagccac ttcagctgct gttatgactg tgattccaaa ccttggaagc agtgatgtgt   180
atttggctta ccttcctttta gctcacgttt ttgagctagc tgccgagacc gtaatgttga   240
ctgcaggtgc ttgtattggt tatggctcag ctctcacatt gacggacact tctaacaaag   300
tcatgaaggg gaccaaggga gatgctacag ttttaaaacc tactttaatg gcagcagttc   360
cagccattct ggatcgtgtt cgggatggtg ttatgaagaa ggttgaggag aaggcaggtt   420
ctgccaagaa acttttccac attggcttta accgtcgatt ggctgctatg aaggtagct    480
ggtttggagc ttggggtcta gagaaacaat tgtgggatat cattatattt aaaaaggtga   540
gggctgtgct tggcggagat atccgtttca tgctttgcgg tggtgctcct ctatcaggag   600
atactcaaag atttatcaac atttgtatgg gagctcctat tggtcaaggg tatggcttga   660
cagaaacatt tgctggagct actttctctg agtgggatga tccttctgtt gggcgtgttg   720
gtccacctct tcctt                                                    735
```

<210> SEQ ID NO 10
<211> LENGTH: 438
<212> TYPE: DNA
<213> ORGANISM: Ghost Chili Pepper

<400> SEQUENCE: 10

```
ctcggggaga agtaggtgtt ggtccacctc ttccttgttc ctacataaag cttgttactt    60
gggaagaagg aggttacaga atagttgata agcctatgcc tcggggagaa gtagttgttg   120
gtggatgcag catcactgct ggttacttca acaatgagga caaaactaat gaggtttata   180
aggttgatga gagaggcatg cgctggttct atactggtga cattggaagg tttcatcccg   240
atggatgcat tgaaattatt gatagaaaga agatatcgt taagcttcag cacggggagt   300
atatctcact tggaaaggtt gaggcagcac ttttatcaag tgattatgtg gaaagcatca   360
tggtctacgc ggaccccttc cacaattatt gtgtagcttt aattgtccct tcacgccagg   420
tgcttgagaa atggtccc                                                 438
```

<210> SEQ ID NO 11
<211> LENGTH: 808
<212> TYPE: DNA
<213> ORGANISM: Ghost Chili Pepper

<400> SEQUENCE: 11

```
aatccatata cgagtacagt ggagagactg accagctatg attatatctc caaaaattat    60
gggtcatctg gggttactgg tgcagttttt attgccatta ttatgccaat aatcctctcc   120
atgttactta tggggaagaa gaaggcaaaa cagagaggtg ttccggttca agttggtggt   180
gaggcaggtc ttgcaatgcg caatgttaaa tcagcaagat tagttgaagt tccttgggaa   240
ggggctacaa ctgtaccagc tctatttgag cagtcttgca aaaaacattc ttctgatcgc   300
tgtcttggaa ctagaaaact agttagcagg gactttgtta ctgcaagtga tggaaggaag   360
tttgagaaac ttcacttggg ggagtatcag tgggaatctt atggacaagt atttgatcgc   420
```

-continued

| | | | | | |
|---|---|---|---|---|---|
| acttgcaact | ttgcctctgg | tcttattaaa | tttggtcatg | atgtggacac | tcacgctgct | 480 |
| atctttgcag | aaactcgtcc | agagtggatc | attgcctttc | agggatgctt | ccggcagaat | 540 |
| gttactgttg | ttaccattta | tgcttccttg | ggtgatgatg | cactcattca | ttcactcaat | 600 |
| gagacccaag | tatctacatt | gatatgtgat | gccaagcaac | tgaaaaaagt | ggcttctgtt | 660 |
| agttcgagcc | tgaaaaccat | caagaatgtc | atctattttg | aggatgacga | gacggcaata | 720 |
| gattccacaa | atattgacag | ctggaggatg | tcgtctttct | cagcagttga | aaagctgggt | 780 |
| aaaaatagtc | ctattcagcc | aagactgc | | | | 808 |

<210> SEQ ID NO 12
<211> LENGTH: 658
<212> TYPE: PRT
<213> ORGANISM: Capsicum annuum

<400> SEQUENCE: 12

Met Ala Thr Asp Lys Phe Ile Ile Glu Val Glu Ser Ala Lys Pro Ala
1               5                   10                  15

Lys Asp Gly Arg Pro Ser Met Gly Pro Val Tyr Arg Ser Ile Phe Ala
            20                  25                  30

Lys His Gly Phe Pro Pro Ile Pro Gly Leu Asp Ser Cys Trp Asp
        35                  40                  45

Ile Phe Arg Met Ser Val Glu Lys Tyr Pro Asn Asn Arg Met Leu Gly
    50                  55                  60

Arg Arg Glu Ile Val Asp Gly Lys Pro Gly Lys Tyr Val Trp Met Ser
65                  70                  75                  80

Tyr Lys Glu Val Tyr Asp Ile Val Ile Lys Val Gly Asn Ser Ile Arg
                85                  90                  95

Ser Ile Gly Val Asp Val Gly Asp Lys Cys Gly Ile Tyr Gly Ala Asn
            100                 105                 110

Cys Pro Glu Trp Ile Ile Ser Met Glu Ala Cys Asn Ala His Gly Leu
        115                 120                 125

Tyr Cys Val Pro Leu Tyr Asp Thr Leu Gly Ala Gly Ala Val Glu Phe
    130                 135                 140

Ile Ile Ser His Ala Glu Val Thr Ile Ala Phe Val Glu Glu Lys Lys
145                 150                 155                 160

Leu Pro Glu Leu Leu Lys Thr Phe Pro Asn Ala Ser Lys Tyr Leu Lys
                165                 170                 175

Thr Ile Val Ser Phe Gly Lys Val Thr Pro Glu Gln Lys Lys Glu Leu
            180                 185                 190

Glu Glu Phe Gly Val Val Leu Tyr Ser Trp Asp Glu Phe Leu Gln Leu
        195                 200                 205

Gly Ser Gly Lys Gln Phe Asp Leu Pro Val Lys Lys Glu Asp Ile
    210                 215                 220

Cys Thr Ile Met Tyr Thr Ser Gly Thr Thr Gly Asp Pro Lys Gly Val
225                 230                 235                 240

Leu Ile Ser Asn Thr Ser Ile Val Thr Leu Ile Ala Gly Val Arg Arg
                245                 250                 255

Phe Leu Gly Ser Val Asp Glu Ser Leu Asn Val Asp Asp Val Tyr Leu
            260                 265                 270

Ser Tyr Leu Pro Leu Ala His Ile Phe Asp Arg Val Ile Glu Glu Cys
        275                 280                 285

Phe Ile His His Gly Ala Ser Ile Gly Phe Trp Arg Gly Asp Val Lys
    290                 295                 300

Leu Leu Thr Glu Asp Ile Gly Glu Leu Lys Pro Thr Val Phe Cys Ala
305                 310                 315                 320

Val Pro Arg Val Leu Asp Arg Ile Tyr Ser Gly Leu Gln Gln Lys Ile
            325                 330                 335

Ala Ala Gly Gly Phe Leu Lys Ser Thr Leu Phe Asn Leu Ala Tyr Ala
            340                 345                 350

Tyr Lys His His Asn Leu Lys Lys Gly Arg Lys His Phe Glu Ala Ser
        355                 360                 365

Pro Leu Ser Asp Lys Val Val Phe Ser Lys Val Lys Glu Gly Leu Gly
    370                 375                 380

Gly Arg Val Arg Leu Ile Leu Ser Gly Ala Ala Pro Leu Ala Ala His
385                 390                 395                 400

Val Glu Ala Phe Leu Arg Val Val Ala Cys Cys His Val Leu Gln Gly
                405                 410                 415

Tyr Gly Leu Thr Glu Thr Cys Ala Gly Thr Phe Val Ser Leu Pro Asn
            420                 425                 430

Arg Tyr Asp Met Leu Gly Thr Val Gly Pro Val Pro Asn Val Asp
        435                 440                 445

Val Cys Leu Glu Ser Val Pro Glu Met Ser Tyr Asp Ala Leu Ser Ser
450                 455                 460

Thr Pro Arg Gly Glu Val Cys Val Arg Gly Asp Ile Leu Phe Ser Gly
465                 470                 475                 480

Tyr Tyr Lys Arg Glu Asp Leu Thr Lys Glu Val Met Ile Asp Gly Trp
                485                 490                 495

Phe His Thr Gly Asp Val Gly Trp Gln Pro Asn Gly Ser Leu Lys
            500                 505                 510

Ile Ile Asp Arg Lys Lys Asn Ile Phe Lys Leu Ser Gln Gly Glu Tyr
            515                 520                 525

Val Ala Val Glu Asn Leu Glu Asn Ile Tyr Gly Asn Asn Pro Ile Ile
530                 535                 540

Asp Ser Ile Trp Ile Tyr Gly Asn Ser Phe Glu Ser Phe Leu Val Ala
545                 550                 555                 560

Val Ile Asn Pro Asn Gln Arg Ala Val Glu Gln Trp Ala Glu Val Asn
                565                 570                 575

Gly Leu Ser Gly Asp Phe Ala Ser Leu Cys Glu Lys Pro Glu Val Lys
            580                 585                 590

Glu Tyr Ile Leu Arg Glu Leu Thr Lys Thr Gly Lys Glu Lys Lys Leu
        595                 600                 605

Lys Gly Phe Glu Phe Leu Lys Ala Val His Leu Asp Pro Val Pro Phe
610                 615                 620

Asp Met Glu Arg Asp Leu Leu Thr Pro Thr Phe Lys Lys Arg Pro
625                 630                 635                 640

Gln Leu Leu Lys Tyr Tyr Lys Asp Val Ile Asp Ser Met Tyr Lys Gly
                645                 650                 655

Thr Lys

<210> SEQ ID NO 13
<211> LENGTH: 658
<212> TYPE: PRT
<213> ORGANISM: Ghost Chili Pepper

<400> SEQUENCE: 13

Met Ala Thr Asp Lys Phe Ile Ile Glu Val Glu Ser Ala Lys Pro Ala
1               5                   10                  15

```
Lys Asp Gly Arg Pro Ser Met Gly Pro Val Tyr Arg Ser Ile Phe Ala
                20                  25                  30

Lys His Gly Phe Pro Pro Ile Pro Gly Leu Asp Ser Cys Trp Asp
        35                  40                  45

Ile Phe Arg Met Ser Val Glu Lys Tyr Pro Asn Asn Arg Met Leu Gly
 50                  55                  60

Arg Arg Glu Ile Val Asp Gly Lys Pro Gly Lys Tyr Val Trp Met Ser
 65                  70                  75                  80

Tyr Lys Glu Val Tyr Asp Ile Val Ile Lys Val Gly Asn Ser Ile Arg
                85                  90                  95

Ser Ile Gly Val Asp Val Gly Asp Lys Cys Gly Ile Tyr Gly Ala Asn
                100                 105                 110

Cys Pro Glu Trp Ile Ile Ser Met Glu Ala Cys Asn Ala His Gly Leu
        115                 120                 125

Tyr Cys Val Pro Leu Tyr Asp Thr Leu Gly Ala Gly Ala Val Glu Phe
        130                 135                 140

Ile Ile Ser His Ala Glu Val Thr Ile Ala Phe Val Glu Glu Lys Lys
145                 150                 155                 160

Leu Pro Glu Leu Leu Lys Thr Phe Pro Asn Ala Ser Lys Tyr Leu Lys
                165                 170                 175

Thr Ile Val Ser Phe Gly Lys Val Thr Pro Glu Gln Lys Lys Glu Leu
                180                 185                 190

Glu Glu Phe Gly Val Val Leu Tyr Ser Trp Asp Glu Phe Leu Gln Leu
        195                 200                 205

Gly Ser Gly Lys Gln Phe Asp Leu Pro Val Lys Lys Glu Asp Ile
        210                 215                 220

Cys Thr Ile Met Tyr Thr Ser Gly Thr Thr Gly Asp Pro Lys Gly Val
225                 230                 235                 240

Leu Ile Ser Asn Thr Ser Ile Val Thr Leu Ile Ala Gly Val Arg Arg
                245                 250                 255

Phe Leu Gly Ser Val Asp Glu Ser Leu Asn Val Asp Asp Val Tyr Leu
        260                 265                 270

Ser Tyr Leu Pro Leu Ala His Ile Phe Asp Arg Val Ile Glu Glu Cys
        275                 280                 285

Phe Ile His His Gly Ala Ser Ile Gly Phe Trp Arg Gly Asp Val Lys
        290                 295                 300

Leu Leu Thr Glu Asp Ile Gly Glu Leu Lys Pro Thr Val Phe Cys Ala
305                 310                 315                 320

Val Pro Arg Val Leu Asp Arg Ile Tyr Ser Gly Leu Gln Gln Lys Ile
                325                 330                 335

Ala Ala Gly Gly Phe Leu Lys Ser Thr Leu Phe Asn Leu Ala Tyr Ala
                340                 345                 350

Tyr Lys His His Asn Leu Lys Lys Gly Arg Lys His Phe Glu Ala Ser
        355                 360                 365

Pro Leu Ser Asp Lys Val Phe Ser Lys Val Lys Glu Gly Leu Gly
        370                 375                 380

Gly Arg Val Arg Leu Ile Leu Ser Gly Ala Ala Pro Leu Ala Ala His
385                 390                 395                 400

Val Glu Ala Phe Leu Arg Val Val Ala Cys Cys His Val Leu Gln Gly
                405                 410                 415

Tyr Gly Leu Thr Glu Thr Cys Ala Gly Thr Phe Val Ser Leu Pro Asn
        420                 425                 430

Arg Tyr Asp Met Leu Gly Thr Val Gly Pro Pro Val Pro Asn Val Asp
```

```
                435                 440                 445
Val Cys Leu Glu Ser Val Pro Glu Met Ser Tyr Asp Ala Leu Ser Ser
            450                 455                 460

Thr Pro Arg Gly Glu Val Cys Val Arg Gly Asp Val Leu Phe Ser Gly
465                 470                 475                 480

Tyr Tyr Lys Arg Glu Asp Leu Thr Lys Glu Val Met Ile Asp Gly Trp
                485                 490                 495

Phe His Thr Gly Asp Val Gly Glu Trp Gln Pro Asn Gly Ser Leu Lys
            500                 505                 510

Ile Ile Asp Arg Lys Lys Asn Ile Phe Lys Leu Ser Gln Gly Glu Tyr
            515                 520                 525

Val Ala Val Glu Asn Leu Glu Asn Ile Tyr Gly Asn Asn Pro Ile Ile
            530                 535                 540

Asp Ser Ile Trp Ile Tyr Gly Asn Ser Phe Glu Ser Phe Leu Val Ala
545                 550                 555                 560

Val Ile Asn Pro Asn Gln Arg Ala Val Glu Gln Trp Ala Glu Val Asn
                565                 570                 575

Gly Leu Ser Gly Asp Phe Ala Ser Leu Cys Glu Lys Pro Glu Val Lys
            580                 585                 590

Glu Tyr Ile Leu Arg Glu Leu Thr Lys Thr Gly Lys Glu Lys Lys Leu
            595                 600                 605

Lys Gly Phe Glu Phe Leu Lys Ala Val His Leu Asp Pro Val Pro Phe
            610                 615                 620

Asp Met Glu Arg Asp Leu Leu Thr Pro Thr Phe Lys Lys Lys Arg Pro
625                 630                 635                 640

Gln Leu Leu Lys Tyr Tyr Lys Asp Val Ile Asp Ser Met Tyr Lys Gly
                645                 650                 655

Thr Lys

<210> SEQ ID NO 14
<211> LENGTH: 666
<212> TYPE: PRT
<213> ORGANISM: Arabidopsis thaliana

<400> SEQUENCE: 14

Met Ser Gln Gln Lys Lys Tyr Ile Phe Gln Val Glu Glu Gly Lys Glu
1               5                   10                  15

Gly Ser Asp Gly Arg Pro Ser Val Gly Pro Val Tyr Arg Ser Ile Phe
                20                  25                  30

Ala Lys Asp Gly Phe Pro Asp Pro Ile Glu Gly Met Asp Ser Cys Trp
            35                  40                  45

Asp Val Phe Arg Met Ser Val Glu Lys Tyr Pro Asn Asn Pro Met Leu
    50                  55                  60

Gly Arg Arg Glu Ile Val Asp Gly Lys Pro Gly Lys Tyr Val Trp Gln
65                  70                  75                  80

Thr Tyr Gln Glu Val Tyr Asp Ile Val Met Lys Leu Gly Asn Ser Leu
                85                  90                  95

Arg Ser Val Gly Val Lys Asp Glu Ala Lys Cys Gly Ile Tyr Gly Ala
            100                 105                 110

Asn Ser Pro Glu Trp Ile Ile Ser Met Glu Ala Cys Asn Ala His Gly
            115                 120                 125

Leu Tyr Cys Val Pro Leu Tyr Asp Thr Leu Gly Ala Asp Ala Val Glu
    130                 135                 140

Phe Ile Ile Ser His Ser Glu Val Ser Ile Val Phe Val Glu Glu Lys
```

-continued

```
                145                 150                 155                 160
Lys Ile Ser Glu Leu Phe Lys Thr Cys Pro Asn Ser Thr Glu Tyr Met
                    165                 170                 175
Lys Thr Val Val Ser Phe Gly Gly Val Ser Arg Glu Gln Lys Glu Glu
                    180                 185                 190
Ala Glu Thr Phe Gly Leu Val Ile Tyr Ala Trp Asp Glu Phe Leu Lys
                    195                 200                 205
Leu Gly Glu Gly Lys Gln Tyr Asp Leu Pro Ile Lys Lys Ser Asp
                210                 215                 220
Ile Cys Thr Ile Met Tyr Thr Ser Gly Thr Thr Gly Asp Pro Lys Gly
225                 230                 235                 240
Val Met Ile Ser Asn Glu Ser Ile Val Thr Leu Ile Ala Gly Val Ile
                    245                 250                 255
Arg Leu Leu Lys Ser Ala Asn Glu Ala Leu Thr Val Lys Asp Val Tyr
                    260                 265                 270
Leu Ser Tyr Leu Pro Leu Ala His Ile Phe Asp Arg Val Ile Glu Glu
                    275                 280                 285
Cys Phe Ile Gln His Gly Ala Ala Ile Gly Phe Trp Arg Gly Asp Val
                    290                 295                 300
Lys Leu Leu Ile Glu Asp Leu Ala Glu Leu Lys Pro Thr Ile Phe Cys
305                 310                 315                 320
Ala Val Pro Arg Val Leu Asp Arg Val Tyr Ser Gly Leu Gln Lys Lys
                    325                 330                 335
Leu Ser Asp Gly Gly Phe Leu Lys Lys Phe Ile Phe Asp Ser Ala Phe
                    340                 345                 350
Ser Tyr Lys Phe Gly Tyr Met Lys Lys Gly Gln Ser His Val Glu Ala
                    355                 360                 365
Ser Pro Leu Phe Asp Lys Leu Val Phe Ser Lys Val Lys Gln Gly Leu
                    370                 375                 380
Gly Gly Asn Val Arg Ile Ile Leu Ser Gly Ala Ala Pro Leu Ala Ser
385                 390                 395                 400
His Val Glu Ser Phe Leu Arg Val Val Ala Cys Cys His Val Leu Gln
                    405                 410                 415
Gly Tyr Gly Leu Thr Glu Ser Cys Ala Gly Thr Phe Val Ser Leu Pro
                    420                 425                 430
Asp Glu Leu Gly Met Leu Gly Thr Val Gly Pro Pro Val Pro Asn Val
                    435                 440                 445
Asp Ile Arg Leu Glu Ser Val Pro Glu Met Glu Tyr Asp Ala Leu Ala
                    450                 455                 460
Ser Thr Ala Arg Gly Glu Ile Cys Ile Arg Gly Lys Thr Leu Phe Ser
465                 470                 475                 480
Gly Tyr Tyr Lys Arg Glu Asp Leu Thr Lys Glu Val Leu Ile Asp Gly
                    485                 490                 495
Trp Leu His Thr Gly Asp Val Gly Glu Trp Gln Pro Asp Gly Ser Met
                    500                 505                 510
Lys Ile Ile Asp Arg Lys Lys Asn Ile Phe Lys Leu Ser Gln Gly Glu
                    515                 520                 525
Tyr Val Ala Val Glu Asn Ile Glu Asn Ile Tyr Gly Glu Val Gln Ala
                    530                 535                 540
Val Asp Ser Val Trp Val Tyr Gly Asn Ser Phe Glu Ser Phe Leu Ile
545                 550                 555                 560
Ala Ile Ala Asn Pro Asn Gln His Ile Leu Glu Arg Trp Ala Ala Glu
                    565                 570                 575
```

```
Asn Gly Val Ser Gly Asp Tyr Asp Ala Leu Cys Gln Asn Glu Lys Ala
            580                 585                 590

Lys Glu Phe Ile Leu Gly Glu Leu Val Lys Met Ala Lys Glu Lys Lys
        595                 600                 605

Met Lys Gly Phe Glu Ile Ile Lys Ala Ile His Leu Asp Pro Val Pro
        610                 615                 620

Phe Asp Met Glu Arg Asp Leu Leu Thr Pro Thr Phe Lys Lys Lys Arg
625                 630                 635                 640

Pro Gln Leu Leu Lys Tyr Tyr Gln Ser Val Ile Asp Glu Met Tyr Lys
                645                 650                 655

Thr Ile Asn Ala Lys Phe Ala Ser Arg Gly
            660                 665
```

<210> SEQ ID NO 15
<211> LENGTH: 666
<212> TYPE: PRT
<213> ORGANISM: Arabidopsis thaliana

<400> SEQUENCE: 15

```
Met Thr Ser Gln Lys Arg Phe Ile Phe Glu Val Glu Ala Ala Lys Glu
1               5                   10                  15

Ala Thr Asp Gly Asn Pro Ser Val Gly Pro Val Tyr Arg Ser Thr Phe
            20                  25                  30

Ala Gln Asn Gly Phe Pro Asn Pro Ile Asp Gly Ile Gln Ser Cys Trp
        35                  40                  45

Asp Ile Phe Arg Thr Ala Val Glu Lys Tyr Pro Asn Asn Arg Met Leu
    50                  55                  60

Gly Arg Arg Glu Ile Ser Asn Gly Lys Ala Gly Lys Tyr Val Trp Lys
65                  70                  75                  80

Thr Tyr Lys Glu Val Tyr Asp Ile Val Ile Lys Leu Gly Asn Ser Leu
                85                  90                  95

Arg Ser Cys Gly Ile Lys Glu Gly Glu Lys Cys Gly Ile Tyr Gly Ile
            100                 105                 110

Asn Cys Cys Glu Trp Ile Ile Ser Met Glu Ala Cys Asn Ala His Gly
        115                 120                 125

Leu Tyr Cys Val Pro Leu Tyr Asp Thr Leu Gly Ala Gly Ala Val Glu
    130                 135                 140

Phe Ile Ile Ser His Ala Glu Val Ser Ile Ala Phe Val Glu Glu Lys
145                 150                 155                 160

Lys Ile Pro Glu Leu Phe Lys Thr Cys Pro Asn Ser Thr Lys Tyr Met
                165                 170                 175

Lys Thr Val Val Ser Phe Gly Val Lys Pro Glu Gln Lys Glu Glu
            180                 185                 190

Ala Glu Lys Leu Gly Leu Val Ile His Ser Trp Asp Glu Phe Leu Lys
        195                 200                 205

Leu Gly Glu Gly Lys Gln Tyr Glu Leu Pro Ile Lys Pro Ser Asp
    210                 215                 220

Ile Cys Thr Ile Met Tyr Thr Ser Gly Thr Thr Gly Asp Pro Lys Gly
225                 230                 235                 240

Val Met Ile Ser Asn Glu Ser Ile Val Thr Ile Thr Gly Val Met
                245                 250                 255

His Phe Leu Gly Asn Val Asn Ala Ser Leu Ser Glu Lys Asp Val Tyr
            260                 265                 270

Ile Ser Tyr Leu Pro Leu Ala His Val Phe Asp Arg Ala Ile Glu Glu
```

-continued

```
                275                 280                 285
Cys Ile Ile Gln Val Gly Gly Ser Ile Gly Phe Trp Arg Gly Asp Val
290                 295                 300
Lys Leu Leu Ile Glu Asp Leu Gly Glu Leu Lys Pro Ser Ile Phe Cys
305                 310                 315                 320
Ala Val Pro Arg Val Leu Asp Arg Val Tyr Thr Gly Leu Gln Gln Lys
                325                 330                 335
Leu Ser Gly Gly Gly Phe Phe Lys Lys Val Phe Asp Val Ala Phe
                340                 345                 350
Ser Tyr Lys Phe Gly Asn Met Lys Lys Gly Gln Ser His Val Ala Ala
                355                 360                 365
Ser Pro Phe Cys Asp Lys Leu Val Phe Asn Lys Val Lys Gln Gly Leu
370                 375                 380
Gly Gly Asn Val Arg Ile Ile Leu Ser Gly Ala Ala Pro Leu Ala Ser
385                 390                 395                 400
His Ile Glu Ser Phe Leu Arg Val Val Ala Cys Cys Asn Val Leu Gln
                405                 410                 415
Gly Tyr Gly Leu Thr Glu Ser Cys Ala Gly Thr Phe Ala Thr Phe Pro
                420                 425                 430
Asp Glu Leu Asp Met Leu Gly Thr Val Gly Pro Val Pro Asn Val
435                 440                 445
Asp Ile Arg Leu Glu Ser Val Pro Glu Met Asn Tyr Asp Ala Leu Gly
                450                 455                 460
Ser Thr Pro Arg Gly Glu Ile Cys Ile Arg Gly Lys Thr Leu Phe Ser
465                 470                 475                 480
Gly Tyr Tyr Lys Arg Glu Asp Leu Thr Lys Glu Val Phe Ile Asp Gly
                485                 490                 495
Trp Leu His Thr Gly Asp Val Gly Glu Trp Gln Pro Asn Gly Ser Met
                500                 505                 510
Lys Ile Ile Asp Arg Lys Lys Asn Ile Phe Lys Leu Ala Gln Gly Glu
                515                 520                 525
Tyr Val Ala Val Glu Asn Leu Glu Asn Val Tyr Ser Gln Val Glu Val
                530                 535                 540
Ile Glu Ser Ile Trp Val Tyr Gly Asn Ser Phe Glu Ser Phe Leu Val
545                 550                 555                 560
Ala Ile Ala Asn Pro Ala Gln Gln Thr Leu Glu Arg Trp Ala Val Glu
                565                 570                 575
Asn Gly Val Asn Gly Asp Phe Asn Ser Ile Cys Gln Asn Ala Lys Ala
                580                 585                 590
Lys Ala Phe Ile Leu Gly Glu Leu Val Lys Thr Ala Lys Glu Asn Lys
                595                 600                 605
Leu Lys Gly Phe Glu Ile Ile Lys Asp Val His Leu Glu Pro Val Ala
                610                 615                 620
Phe Asp Met Glu Arg Asp Leu Leu Thr Pro Thr Tyr Lys Lys Lys Arg
625                 630                 635                 640
Pro Gln Leu Leu Lys Tyr Tyr Gln Asn Val Ile His Glu Met Tyr Lys
                645                 650                 655
Thr Thr Lys Glu Thr Leu Ala Ser Gly Gln
                660                 665
```

METHODS OF USING ACYL-COA SYNTHETASE FOR BIOSYNTHETIC PRODUCTION OF ACYL-COAS

CROSS-REFERENCE TO RELATED APPLICATIONS

This application is a national stage filing under U.S.C. § 371 of PCT International Application No. PCT/US2014/063695, with an international filing date of Nov. 3, 2014, which claims priority to U.S. Provisional Patent application No. 61/898,944 filed on Nov. 1, 2013, the contents of each of which are incorporated by reference herein in their entirety.

TECHNICAL FIELD

This disclosure has applicability in the food, medicinal, and pharmacological industries. This disclosure relates generally to a method for the biosynthetic production of acyl-CoAs utilizing acyl-CoA synthetase (ACS).

BACKGROUND OF THE DISCLOSURE

Background Art

Capsaicin, 8-methyl-N-vanillyl-trans-6-nonenamide, is a secondary metabolite produced in hot peppers (*Capsicum* spp.) that is responsible for their pungent flavor. As noted in FIG. 1, Capsaicin is believed to be synthesized by capsaicin synthase (CS), an acyltransferase that transfers the 8-methylnonenoyl moiety from 8-methylnonenoyl-CoA to vanillylamine to form an amide conjugate, although the gene encoding CS has not been unambiguously identified at the time of the filing of the correlative provisional application. Again, as detailed in FIG. 1, the substrate for CS, 8-methylnonenoyl-CoA, is derived from 8-methyl-trans-6-nonenoic acid through the activity of an acyl-CoA synthetase (ACS).

ACS catalyzes the conversion of a carboxylic acid to its acyl-CoA thioester through an ATP-dependent two-step reaction. In the first step, the free fatty acid is converted into an acyl-AMP intermediate with the release of pyrophosphate. In the second step, the activated acyl group is coupled to the thiol group of CoA, releasing AMP and the acyl-CoA product (Groot et al., 1976). ACS and other related proteins are characterized by a highly conserved 12-amino acid sequence that forms the core of an AMP binding motif (PROSITE PS00455). About 44 putative ACS genes have been identified in the model plant *Arabidopsis thaliana* (Shockey et al., 2003). Currently, about half of them have known biochemical functions which include long-chain acyl-CoA synthetases, acyl-ACP synthetases, 4-coumaroyl-CoA ligases, acetyl-CoA synthetase, OPC-8:0 CoA Ligase, succinylbenzoyl-CoA ligase, malonyl-CoA synthetase, and oxalyl-CoA synthetase (Shockey et al., 2003; Koo et al., 2005; Koo et al., 2006; Kim et al., 2008; Lin and Oliver, 2008; Chen et al., 2011; Foster et al., 2012). In *Capsicum annuum*, three full-length putative ACS genes have been cloned (Lee et al., 2001; Mazourek et al., 2009). However, no biochemical activity has been ascribed to any of these proteins.

Applicants set out to identify the genes involved in capsaicin biosynthesis, particularly ACS. Since the hot pepper genome sequence was not available at the time when the study was initiated, applicants employed RNA Sequencing (RNA-Seq) technology for transcriptome analysis of the green fruits of the ghost chili pepper, an interspecies hybrid of *C. chinense* and *C. frutescens*. RNAseq experiment was performed by MOgene, LC (St Louis, Mo.). Applicants obtained about 18,987 contigs through the de novo assembly of the raw RNAseq data, 33 of which were annotated as acyl-CoA synthetase-like proteins. Among these contigs, Comp2147-1 showed a good match to CaSIG4 (FIG. 2A-C), a pathogen-inducible cDNA encoding a putative acyl-CoA synthetase from *Capsicum annuum* (Lee et al., 2001). In addition, Comp66462 and Comp79520 mapped to pepper ACS1 (GenBank: EU616571) (FIG. 3A-C), and Comp 167_c0, Comp167_c1 and Comp 46218 mapped to pepper ACS2 (GenBank: EU616572) (FIGS. 4A and B). Accordingly, ACS1 and ACS2 are two candidates for the acyl-CoA synthetase that exports fatty acids from the plastid (Mazourek et al., 2009).

Applicants demonstrate that ACS1 is a medium/long-chain acyl-CoA synthetase that converts 8-methyl-trans-6-nonenoic acid to the corresponding 8-methyl-6-nonenoyl-CoA, a key intermediate in the capsaicin biosynthetic pathway. Applicants disclose in the application herein methods of using ACS, particularly ACS1, for the biosynthetic production of acyl-CoAs.

BRIEF SUMMARY OF DISCLOSURE

The disclosure addresses the technical issue of producing acyl-CoAs in a cellular system, such as yeast or bacteria. Applicants have isolated the gene for ACS and uniquely expressed it in a cellular system that facilitates the production of acyl-CoAs. A particular acyl-CoA, 8-methyl-6-nonenoyl-CoA, is a necessary substrate for capsaicin synthase (CS), which would then produce capsaicin. Thus, this disclosure provides for the industrial production of 8-methyl-6-nonenoyl-CoA and helps to facilitate subsequent production of capsaicin.

The present disclosure is a biosynthetic method of making carboxyl CoAs from medium/long-chain carboxylic acid including expressing an ACS in a cellular system, feeding a long-chain carboxylic acid to the cellular system, growing the cellular system in a medium, and producing carboxyl CoAs.

Another embodiment is a biosynthetic method of making 8-methylnonenoyl-CoA comprising expressing an ACS in a cellular system, feeding 8-methyl-trans-6-nonenoic acid to the cellular system, growing the cellular system in a medium, and producing 8-methylnonenoyl-CoA.

BRIEF DESCRIPTIONS OF THE DRAWINGS

For a better understanding of the present disclosure, reference may be made to the accompanying drawings in which:

FIGS. 2A-2C show sequence comparison between Comp2147-1 (SEQ ID NO: 4) and CaSIG4 (SEQ ID NO: 3) (GenBank: AF354454).

FIGS. 3A-3C show sequence comparison between Comp66462 (SEQ ID NO: 6), Comp79520 (SEQ ID NO: 7) and ACS1 (SEQ ID NO: 5) (GenBank: EU616571).

Figure 4A shows sequence comparison between Comp167_c0 (SEQ ID NO: 9), Comp46218 (SEQ ID NO: 11) and ACS2 (SEQ ID NO: 8) (GenBank: EU616572). FIG.

4B shows sequence comparison between Comp167_cl (SEQ ID NO: 10) and ACS2 (SEQ ID NO: 8) (GenBank: EU616572).

FIG. 5 shows sequence comparison between ghost pepper ACS1 (SEQ ID NO: 13) and ACS1 (SEQ ID NO: 12) (GenBank: ACF17663).

FIG. 6 shows sequence comparison between ghost pepper ACS1 (SEQ ID NO: 13), Arabidopsis LACS4 (SEQ ID NO: 14) (GenBank: AEE84812) and LACS5 (SEQ ID NO: 15) (GenBank: AAM28872).

Figure 1:
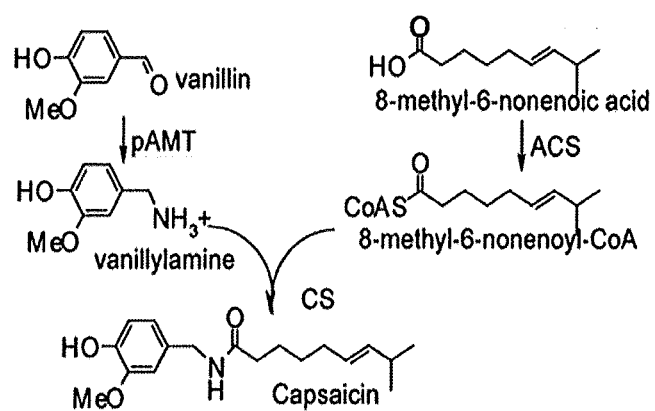
FIG. 1 shows the capsaicin biosynthetic pathway, which includes the reaction by ACS of making 8-methyl-6-nonenoyl-CoA from 8-methyl-6-nonenoic acid. Adapted from Stewart et al. (2007).
Figure 7:
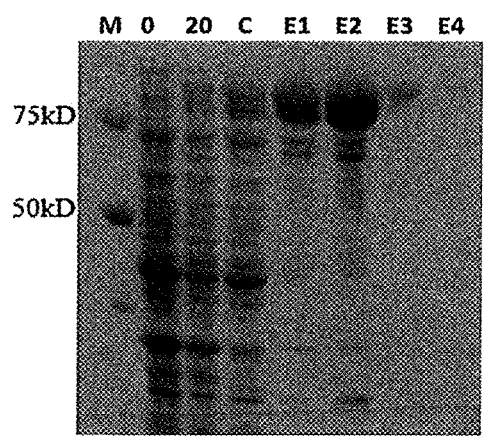

FIG. 7 shows SDS-PAGE analysis of His-SUMO-ACS1 expression in BL21 (DE3) cells. 0, 20: total protein at the time after IPTG induction; C, soluble crude protein extract; E1 to E4, fractions from Ni-NTA column. The molecular weight of ACS1 is ca. 73.5 Kd and that of His-SUMO tag is ca. 12 Kd.

Figure 8:
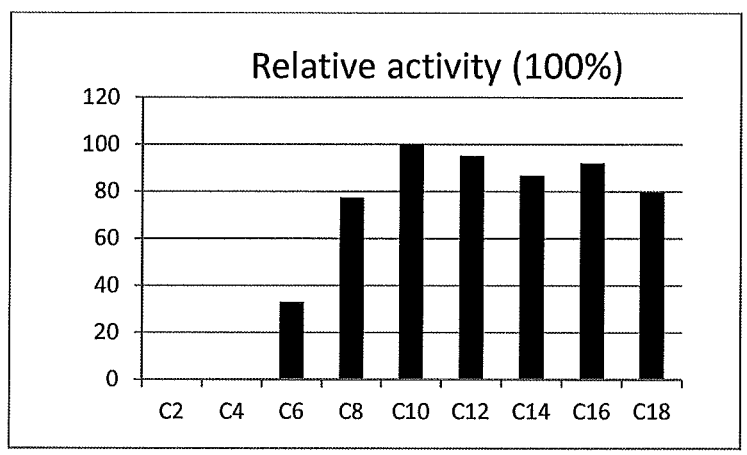

FIG. 8 shows activities of ACS1 against various carboxylic acids. C2, acetic acid; C4, butyric acid; C6, hexanoic acid, C8,caprylic acid; C10, capric acid; C12, lauric acid; C14, myristic acid; C16, palmitic acid; C18, stearic acid. The assay was performed in 100 mM Tri buffer, pH8.0.

Figure 9:
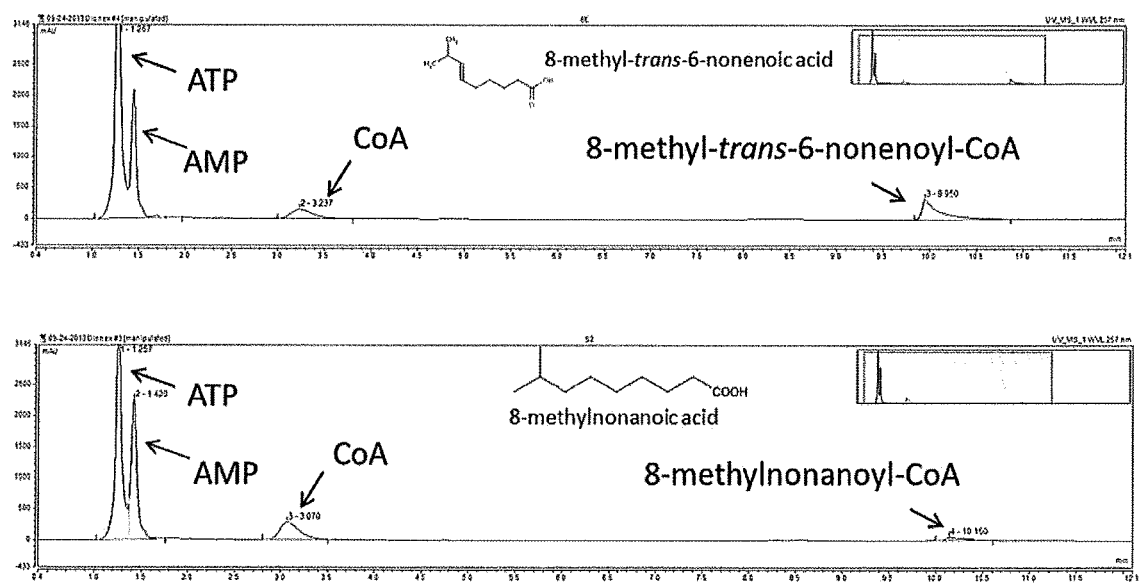

FIG. 9 shows HPLC profiles of enzymatic products of ACS1 with 8-methyl-trans-6-nonenoic acid or 8-methyl nonanoic acid as a substrate, respectively.

FIG. 10 shows MS/MS analysis of purified 8-methyl-trans-6-noneoyl-CoA in negative mode.

FIG. 11 shows MS/MS analysis of purified 8-methylnonaoyl-CoA in negative mode.

Figure 12:
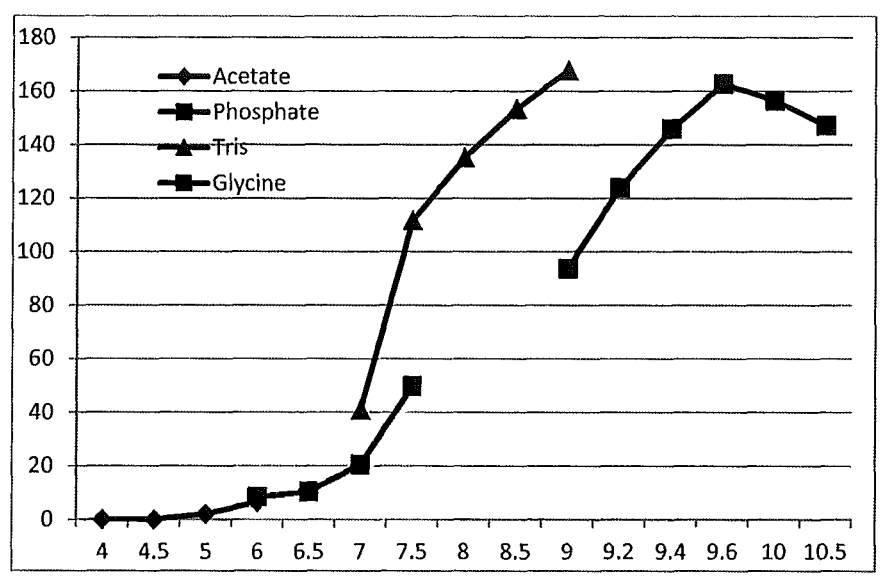

FIG. 12 shows effect pH on the activity of ACS1 against 8-methylnonanoic acid. Four different buffer systems were used for different pH ranges.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

DETAILED DESCRIPTIONS OF THE DISCLOSURE

Definitions
Cellular System
Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.
Growing the Cellular System
Growing includes providing medium that would allow cells to multiply and divide. It also includes providing resources so that cells or cellular components can translate and make recombinant proteins.
Protein Expression
Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

An embodiment of the present disclosure is a biosynthetic method of making carboxyl CoAs from medium to long-chain carboxylic acids comprising expressing an ACS in a cellular system, feeding medium to long-chain carboxylic acids to the cellular system, growing the cellular system in a medium, and producing carboxyl CoAs.

A further embodiment is that the ACS is expressed from ACS1 cloned from ghost chili pepper. An alternative embodiment is that the ACS is expressed from *Arabidopsis* based on LCAS4 or LCAS5. In another embodiment, the ACS is expressed from ACS2 cloned from *Capsicum* spp. Further, the ACS is an ACS that shares a sequence identity of at least 66% with the ACS1 cloned from ghost chili pepper. In another variation, the ACS is an ACS that shares a sequence similarity of at least 97% with the ACS1 cloned from ghost chili pepper.

A further embodiment is that the medium or long-chain carboxylic acid is 8-methyl-trans-6-nonenoic acid. Long chain carboxylic acids generally have 14 to 18 carbons, while medium-chain carboxylic acids generally have 8 to 13 carbons. In one embodiment, the feeding of medium to long-chain carboxylic acid to the cellular system comprises adding the medium to long-chain carboxylic acid to the cellular system. In an alternative embodiment, the feeding of medium to long-chain carboxylic acid to the cellular system comprises expressing the medium to long-chain carboxylic acid from a biosynthetic pathway in the cellular system.

As for the cellular system in the embodiment, it is selected from the group consisting of bacteria, yeast, and a combination thereof, or any cellular system that would allow the biosynthetic production is provided.

An embodiment of the present disclosure is a biosynthetic method of making 8-methylnonenoyl-CoA comprising expressing an ACS in a cellular system, feeding 8-methyl-trans-6-nonenoic acid to the cellular system, growing the cellular system in a medium, and producing 8-methylnonenoyl-CoA. The ACS is expressed from ACS1 cloned from ghost chili pepper. The ACS can be expressed from LCAS4 or LCAS5 cloned from *Arabidopsis*. In another embodiment, the ACS is expressed from ACS2 cloned from *Capsicuni* spp. Further, the ACS is an ACS that shares a sequence identity of at least 66% with the ACS1 cloned from ghost chili pepper. In another variation, the ACS is an ACS that shares a sequence similarity of at least 97% with the ACS1 cloned from ghost chili pepper.

EXAMPLE 1

Producing Acyl-CoAs
Cloning
Applicants amplified ACS1 gene from cDNA of the green fruits of the ghost chili pepper using the primers of ACS1-sumo-F: CGC GAA CAG ATT GGA GGT GCAACAGA-TAAATTTATTATTG (SEQ ID NO: 1) and ACS1-sumo-R: GTG GCG GCC GCT CTA TTA TCACTTGGTACCCTT-GTACAT (SEQ ID NO: 2). The resulting PCR product was purified on 1% agarose gel and mixed with linear pETite N-His SUMO Kan expression vector (Lucigen, Middleton, WI). The DNA mixture was used to transform HI-control 10G chemically competent cells by heat shock (Lucigen). The gene insertion was fully sequenced and the encoded amino acid sequence was aligned with that of ACS1 (FIG. 5). As shown in FIG. 5, these two sequences are almost identical except Ile476 in *Capsicum annuum* ACS1 is replaced by Val in ghost pepper ACS1. The sequence of ghost pepper ACS1 was used to blast *Arabidopsis* database (*Arabidopsis*.org) and identified LCAS4 and LACS5 as its homologues (FIG. 6). As shown in FIG. 6, these three sequences share a sequence identity of 66.7% and a sequence similarity of 97.1%. Both LACS4 and LACS5 have been biochemically characterized as long chain acyl-CoA synthetases that participate in fatty acid and glycerolipid metabolism (Shockey et al., 2002). Recently, LACS4 is demonstrated to be required for the formation of pollen coat lipids in *Arabidopsis* (Jessen et al., 2011).

Expression

Applicants used pETite N-His SUMO-ghost pepper ACS1 to transform HI-Control BL21(DE3) cells (Lucigen) and the expression of His-SUMO-ACS1 was induced by 0.5 mM IPTG at 16° C. for 20 hrs. The fusion protein was purified by Ni-NTA column (FIG. 7). ACS1 has a molecular weight of ca. 73.5 Kd and the size of His-SUMO tag is ca. 12 Kd. The His-SUMO-ghost pepper ACS1 fusion protein on SDS-PAGE migrated close to the predicted size (ca. 85 Kd) (FIG. 7).

Products

Applicants used an HPLC-based method to measure the activity of ghost pepper ACS1 (Chen et al., 2011). Briefly, reaction mixtures (400 μL) contained 0.1 M Tris-HCl, pH 7.5, 2 mM DTT, 5 mM ATP, 10 mM $MgCl_2$, 0.5 mM CoA, 0.1% Triton and 200 μM carboxylic acids. The reaction was initiated by adding 20 μl of purified enzyme and stopped after 30 min by addition of 20 μl al acetic acid. HPLC was performed with Dionex-UltiMate® 3000 LC Systems (Thermo Scientific) using an Acclaim® 120 C18 reversed-phase column (Thermo Scientific; 3 μ, 120 Å, 150×3 mm). The mobile phase consisted of solvent A (0.1% trifluoro-acetic acid) and solvent B (acetonitrile). The gradient elution procedure was as follows: 0 to 5 min, 5% of B; 5 to 9 min, a linear gradient from 5 to 80% of B; 9 to 11 min, 80% of B; 11 to 12 min, 5% of B. The flow rate was 0.6 ml/min. The diode array detector collected data in the 200- to 400-nm range. For detection and quantification of substrate and products, peak areas were measured at 257 nm.

As shown in FIG. 8, ACS1 had activities in various medium against long chain carboxylic acids with the highest activity against capric acid (C10). In contrast, ACS1 did not show any activity against acetic acid (C2) or butyric acid (C4)-short chain carboxylic acid.

Applicants then used 8-methyl-trans-6-nonenoic acid (6E), the endogenous intermediate in capsaicin biosynthetic pathway or its reduced product, 8-methylnonanoic acid (8M), as a substrate to assay ACS1 activity. As shown in FIG. 9, ACS1 showed activities with both substrates with a higher activity for 6E. Applicants collected the corresponding HPLC fractions for the product peaks and dried them over a SpeedVac Concentrator for further MS/MS identification.

Confirmation of Product

Each dried sample was resuspended in 40 μL of 1:1:2 Methanol:Water:Acetonitrile buffer. 10 μL was used for direct infusion using the TriVersa NANOMATE® integrated ion source platform (Advion, Ithaca, NY). The mass spectrometer, LTQ-Orbitrap Velos (Thermo Fisher Scientific, Waltham, MA), was operated in negative ionization mode. The MS survey scan was performed in the FT cell from a mass range of 300 to 2,000 m/z. The resolution was set to 60,000 @ 400 m/z. CID fragmentation was used for MS/MS, and detection was done in the ion trap with an isolation window of 1.5 m/z Fragmentation was performed with normalized collision energies of 35%. As shown in FIGS. 10-11, the MS data match the molecular weight of 8-methyl-trans-6-nonenoyl-CoA and 8-methyl nonanoyl-CoA, respectively.

The pH optimal of ACS1 against 8-methylnonanoic acid was also studied. Acetate, phosphate, Tris and glycine/NaOH buffers were used to provide a pH range from 4.0 to 10.5. As shown in FIG. 12, the optical pH of ACS1 is ca. 9.5.

Accordingly, applicants have identified a novel medium/long chain acyl-CoA synthetase in ghost hot pepper which provides the substrate for capsaicin synthase. In addition, the novel enzyme may also have applications in biofuel industry for making medium-chain fatty acid derivatives.

Additional embodiments include the use of ACS1 to modify the levels of capsaicinoids in pepper plants by overexpressing ACS1 utilizing standard known techniques for overexpression of genes. Another embodiment includes the use of ACS1 to modulate the levels of capsaicinoids in pepper plants by knocking out or knocking down ACS1 utilizing standard known techniques for knocking out or knocking down expression of genes. Again, the overexpression or the knock out/knock down is by standard molecular cellular strategies and techniques known by a person of ordinary skill in the art. Another embodiment includes the use of ACS1 to generate acyl-CoAs and their downstream metabolites including fatty acids involving the expression or overexpression of ACS1. Another variation is the use of ACS1 to modulate the levels of acyl-CoAs and their downstream metabolites including fatty acids comprising knocking out or knocking down ACS1.

The acyl CoAs that are made by the methods could be utilized to make capsaicin, and they would generally be of the medium chain variety. Again, although ACS1 can mediate the conversion of both medium chain- and long chain-carboxylic acids to acyl-CoAs, the medium chain activity is far more important than long chain activity as medium chain activity is the essential component in today's biofuel industry. The other importance as mentioned above for ACS1 is that it can be used to modify the capsaicin levels in plants through transgenic technology. However, ACS1 is not precluded from usage in regards to long chain acyl-CoAs.

In an embodiment, a cellular system, such as a bacterial based system or a yeast based system can be modified to express ACS. The ACS could be ACS1 cloned from ghost pepper. Other ACSs suitable are one based on LCAS4 and LCAS5 from *Arabidopsis*. Other known ACS1 and ACS2 could also be expressed in the cellular systems. Appropriate substrate, such as 8-methyl-trans-6-nonenoic acid and 8-methylnonanoic acid, can then be fed to the cellular system. The substrates could also be expressed as part of a biosynthetic pathway within the cellular system. The cellular system is then incubated allowing for the biosynthetic production of 8-methyl-trans-6-nonenoyl-CoA or 8-methyl nonanoyl-CoA.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Other aspects, objects and advantages of the present disclosure can be obtained from a study of the drawings, the disclosure and the appended claims.

REFERENCES

Chen H, Kim H U, Weng H, Browse J. (2011) Malonyl-CoA synthetase, encoded by ACYL ACTIVATING ENZYME13, is essential for growth and development of *Arabidopsis*. Plant Cell 23: 2247-2262.

Foster J, Kim H U, Nakata P A, Browse J. (2012) A previously unknown oxalyl-CoA synthetase is important for oxalate catabolism in *Arabidopsis*. Plant Cell 24: 1217-1229.

Groot P H, Scholte H R, Hülsmann W C. (1976) Fatty acid activation: Specificity, localization, and function. Adv. Lipid Res. 14: 75-126.

Jessen D, Olbrich A, Küfer J, Kruger A, Hoppert M, Polle A, Fulda M. (2011) Combined activity of LACS1 and LACS4 is required for proper pollen coat formation in *Arabidopsis*. Plant J. 68: 715-726.

Kim H U, van Oostende C, Basset G J, Browse J. (2008) The AAE14 gene encodes the *Arabidopsis* o-succinylbenzoyl-CoA ligase that is essential for phylloquinone synthesis and photosystem-I function. Plant J. 54: 272-283.

Kim S, Park M, Yeom S I, Kim Y M, Lee J M, Lee H A, Seo E, Choi J, Cheong K, Kim K T, Jung K, Lee G W, Oh S K, Bae C, Kim S B, Lee H Y, Kim S Y, Kim M S, Kang B C, Jo Y D, Yang H B, Jeong H J, Kang W H, Kwon J K, Shin C, Lim J Y, Park J H, Huh J H, Kim J S, Kim B D, Cohen O, Paran I, Suh M C, Lee S B, Kim Y K, Shin Y, Noh S J, Park J, Seo Y S, Kwon S Y, Kim H A, Park J M, Kim H J, Choi S B, Bosland P W, Reeves G, Jo S H, Lee B W, Cho H T, Choi H S, Lee M S, Yu Y, Do Choi Y, Park B S, van Deynze A, Ashrafi H, Hill T, Kim W T, Pai H S, Ahn H K, Yeam I, Giovannoni J J, Rose J K, Sorensen I, Lee S J, Kim R W, Choi I Y, Choi B S, Lim J S, Lee Y H, Choi D. (2014) Genome sequence of the hot pepper provides insights into the evolution of pungency in *Capsicum* species. Nature Genetics 46(3):270-278. doi: 10.1038/ng.2877. Epub 2014 Jan. 19. Koo A J, Fulda M, Browse J, Ohlrogge J B. (2005) Identification of a plastid acyl-acyl carrier protein synthetase in *Arabidopsis* and its role in the activation and elongation of exogenous fatty acids. Plant J. 44: 620-632.

Koo A J, Chung H S, Kobayashi Y, Howe G A. (2006) Identification of a peroxisomal acyl-activating enzyme involved in the biosynthesis of jasmonic acid in *Arabidopsis*. J Biol Chem. 281: 33511-33520.

Lee S J, Suh M C, Kim S, Kwon J K, Kim M, Paek K H, Choi D, Kim B D. (2001) Molecular cloning of a novel pathogen-inducible cDNA encoding a putative acyl-CoA synthetase from *Capsicum annum* L. Plant Mol Biol. 46: 661-671.

Lin M, Oliver D J. (2008) The role of acetyl-coenzyme a synthetase in *Arabidopsis*. Plant Physiol. 147: 1822-1829.

Mazourek M, Pujar A, Borovsky Y, Paran I, Mueller L, Jahn M M. (2009) A dynamic interface for capsaicinoid systems biology. Plant Physiol. 150: 1806-1821.

Qin C, Yu C, Shen Y, Fang X, Chen L, Min J, Cheng J, Zhao S, Xu M, Luo Y, Yang Y, Wu Z, Mao L, Wu H, Ling-Hu C, Zhou H, Lin H, González-Morales S, Trejo-Saavedra D L, Tian H, Tang X, Zhao M, Huang Z, Zhou A, Yao X, Cui J, Li W, Chen Z, Feng Y, Niu Y, Bi S, Yang X, Li W, Cai H, Luo X, Montes-Hernández S, Leyva-González MA, Xiong Z, He X, Bai L, Tan S, Tang X, Liu D, Liu J, Zhang S, Chen M, Zhang L, Zhang L, Zhang Y, Liao W, Zhang Y, Wang M, Lv X, Wen B, Liu H, Luan H, Zhang Y, Yang S, Wang X, Xu J, Li X, Li S, Wang J, Palloix A, Bosland P W, Li Y, Krogh A, Rivera-Bustamante R F, Herrera-Estrella L, Yin Y, Yu J, Hu K, Zhang Z. (2014) Whole-genome sequencing of cultivated and wild peppers provides insights into *Capsicum* domestication and specialization. Proc Natl Acad Sci USA. 111(14):5135-5140. doi: 10.1073/pnas.1400975111. Epub 2014 Mar. 3.

Shockey J M, Fulda M S, Browse J A. (2002) *Arabidopsis* contains nine long-chain acyl-coenzyme a synthetase genes that participate in fatty acid and glycerolipid metabolism. Plant Physiol. 129: 1710-1722.

Shockey J M, Fulda M S, Browse J. (2003) *Arabidopsis* contains a large superfamily of acyl-activating enzymes. Phylogenetic and biochemical analysis reveals a new class of acyl-coenzyme a synthetases. Plant Physiol. 132: 1065-1076.

Stewart C Jr, Mazourek M, Stellari G M, O'Connell M, Jahn M. (2007) Genetic control of pungency in *C. chinense* via the Pun1 locus. J Exp Bot. 58: 979-991.

What is claimed is:

1. A biosynthetic method of making 8-methylnonenoyl-CoA comprising:
   expressing a heterologous acyl-CoA synthetase (ACS) in a cellular system;
   feeding 8-methyl-trans-6-nonenoic acid to the cellular system;
   growing the cellular system in a medium; and
   producing 8-methylnonenoyl-CoA,
   wherein the cellular system is bacteria or yeast, and
   wherein the heterologous ACS is ghost chili pepper ACS1.

2. The biosynthetic method of making 8-methylnonenoyl-CoA of claim 1, wherein the feeding 8-methyl-trans-6-nonenoic acid to the cellular system comprises adding the 8-methyl-trans-6-nonenoic acid to the cellular system.

3. The biosynthetic method of making 8-methylnonenoyl-CoA of claim 1, wherein the feeding 8-methyl-trans-6-nonenoic acid to the cellular system comprises producing the 8-methyl-trans-6-nonenoic acid from a biosynthetic pathway in the cellular system.

4. The biosynthetic method of making 8-methylnonenoyl-CoA of claim 1, wherein the cellular system is bacteria.

5. The biosynthetic method of making 8-methylnonenoyl-CoA of claim 1, wherein the cellular system is yeast.

* * * * *